Figure 1:
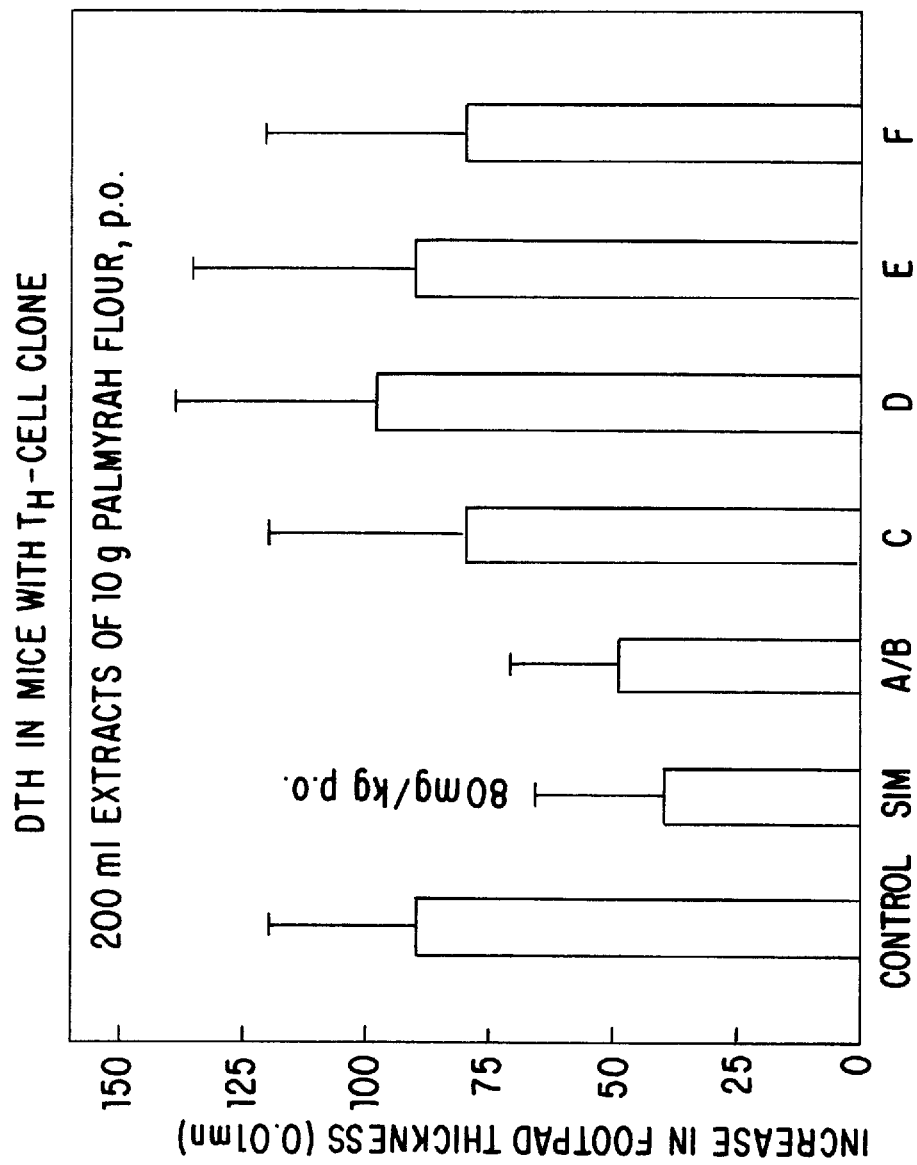

United States Patent [19]
Hiestand et al.

[11] Patent Number: 5,852,005
[45] Date of Patent: Dec. 22, 1998

[54] TETRACYCLIC TRITERPENES

[75] Inventors: Peter Hiestand, Allschwil; Reto Naef, Rheinfelden; Hans-Ulrich Naegeli, Arlesheim; Lukas Oberer, Tenniken; Laszlo Revesz, Therwil; Hans-Jörg Roth, Gipf-Oberfrick, all of Switzerland

[73] Assignee: Novartis AG, Basel, Switzerland

[21] Appl. No.: 776,442

[22] PCT Filed: Jul. 24, 1995

[86] PCT No.: PCT/EP95/02913

§ 371 Date: Jan. 24, 1997

§ 102(e) Date: Jan. 24, 1997

[87] PCT Pub. No.: WO96/03419

PCT Pub. Date: Feb. 8, 1996

[30] Foreign Application Priority Data

Jul. 27, 1994 [GB] United Kingdom ............ 941516

[51] Int. Cl.$^6$ ................. C07J 9/00; C07J 1/00; A61K 31/565; A61K 31/575
[52] U.S. Cl. .......................... 514/169; 552/502
[58] Field of Search .............. 552/502; 514/169

[56] References Cited

U.S. PATENT DOCUMENTS

| | | | |
|---|---|---|---|
| 3,644,421 | 2/1972 | Cross | 260/340.5 |
| 3,868,453 | 2/1975 | Van Kamp et al. | 424/243 |
| 4,057,543 | 11/1977 | Dryden, Jr. et al. | 260/239.57 |
| 4,636,496 | 1/1987 | Brooks et al. | 514/182 |
| 4,755,504 | 7/1988 | Yaguang | 514/26 |

OTHER PUBLICATIONS

Bardon et al., Phytochemistry, (1993), 34(1), pp. 253–259.
Chemical Abstracts, vol. 100, No. 11, 1984, Abstract No. 79597q.
Chemical Abstracts, vol. 118, No. 2, 1993, Abstract No. 11726X.
Chemical Abstracts, vol. 92, No. 23, 1980, Abstract No. 191300e.
Yien–Mei Lee, et al., Chemical & Pharmaceutical Bulletin, vol. 25, No. 6, 1977, pp. 1391–1398.
Hiroshi Saito, et al., Chemical & Pharmaceutical Bulletin, vol. 25, No. 5, 1977, pp. 1017–1025.
Chemical Abstracts, vol. 114, No. 7, 1991, Abstract No. 55458h.
I.R. Lee, et al., Archives of Pharmacal Research, vol. 16, No. 4, Dec. 1993, pp. 331–335.
K. Yasukawa, et al., Oncology, vol. 48, No. 1, 1991, pp. 72–76.
Chemical Abstracts, vol. 123, No. 15, 1995, Abstract No. 188022u.
H. Fujimoto, et al., Chemical & Pharmaceutical Bulletin, vol. 18, No. 7, 1970, Tokyo JP, pp. 1440–1445.
D. A. Mulholland, et al., Phytochemistry, vol. 35, No. 2, 20 Jan. 1994, pp. 542–544.
R. A. Hill, et al., Dictionary of Steroids, 1991, pp. 218–222 and p. 551.
Han, et al., Phytochemistry, No. 16, 1997, p. 1075.
B.L. Poehland, et al., Journal of Natural Products, vol. 50, No. 4, 1987, pp. 706–713.
R. Tanaka, et al., Phytochemistry, vol. 26, No. 12, 1987, pp. 3365–3366.
Corey and Virgil, J. Am. Chem. Soc., vol. 113, 1991, pp. 4025–4026.

(List continued on next page.)

Primary Examiner—S. Mark Clardy
Assistant Examiner—Sabiha N. Qazi
Attorney, Agent, or Firm—Carol A. Loeschorn

[57] ABSTRACT

The present invention relates to 17 α-dammara compounds having immunosuppressant and antiinflammatory activity and which are useful as pharmaceuticals, particularly for use as immunosuppressant and antiinflammatory agents. Specific 17 α-dammara compounds are included per se, for example the compound of formula IC, i.e. 17 α-23-(E)-dammara-20, 23-dien-3β, 25-diol, which may be obtained from the flour of the shoots of the Palmyrah palm, *Borassus flabellifer L*. In addition, processes for the synthesis of this and other dammara compounds and intermediates thereof are described.

15 Claims, 3 Drawing Sheets

OTHER PUBLICATIONS

J.–F. Mayaux, et al., Proc. Natl. Acad. Sci., USA, vol. 91, Apr. 1994, pp. 3564–3568.

S. P. Gunasekera, et al., Journal of Natural Products, vol. 52, No. 4, Jul.–Aug. 1989, pp. 757–761.

J. Asakawa, et al., Tetrahedron, vol. 33, 1977, pp. 1935–1939.

TETRACYCLIC TRITERPENES

This application has been filed under 35 USC 371 as a national stage application of PCT/EP95/02913 filed Jul. 24, 1995 published as WO96/03419 Feb. 8, 1996. The present invention relates to dammara compounds and to pharmaceutical uses thereof. The dammara compounds comprise a recognized compound group of the triterpene class and are characterised by a tetracyclic core structure of formula I.

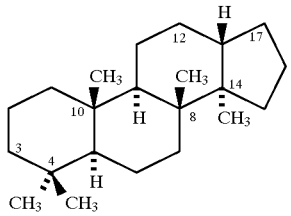

In the known dammara compounds this core structure is commonly substituted, generally mono-substituted, at the 3-position, e.g. by hydroxy (dammar-3-ols) or oxo (dammar-3-ones). Dammara compounds are also commonly substituted, generally mono-substituted, at the 17-position, e.g. as in the case of the dammarenes which are found in Ginseng root and other plant material and in which the 17-position commonly bears a hydrocarbyl residue comprising one or more, e.g. 1 or 2, alkene (—C=C—) linkages. Most typically in the case of the dammarenes, the 17-hydrocarbyl substituent comprises a $C_8$-alkenyl or -alkadienyl residue which may be further substituted, e.g. by one or more hydroxy groups. Dammara compounds may also bear one or more further substituents, commonly hydroxy groups, at other positions on the core structure or may incorporate one or more unsaturated linkages, e.g. double bonds, within the core structure. In the dammara compounds, however, the cyclic structure, stereochemical configuration as well as distribution of methyl groups at the 4-, 10-, 8- and -14 positions shown in formula I remains unaltered.

In accordance with the present invention it has now been found that dammara compounds have desirable pharmaceutical, in particular immunosuppressive and antiinflammatory, properties.

Accordingly the invention provides in a first aspect:

a¹) A dammara compound for use as a pharmaceutical, e.g. for use as an immunosuppressant or an antiinflammatory agent;

a²) A dammara compound for the preparation of a medicament for therapeutic application as an immunosuppressant or an antiinflammatory agent; and/or a³) A method of treating a subject in need of immunosuppressive or antiinflammatory therapy which comprises administering an effective amount of a dammara compound to said subject.

Specific immunosuppressive and/or antiinflammatory indications or conditions comprised in the above definitions a¹) to a³) include, in particular, any of those hereinafter specifically set forth.

By the term "dammara compound" as used herein is meant a compound comprising the characteristic core structure of formula I as herein above illustrated, i.e. having the particular cyclic structure, stereochemical configuration and distribution of methyl substituents shown in formula I. To the extent that stereochemical configuration shown in formula I remains unaltered, the term is to be understood as embracing compounds in which the formula I core structure bears one or more additional substituents, in particular at the 3- and/or 17-position, as well as compounds in which one or more of the carbon-carbon linkages comprising the core structure is/are unsaturated, e.g. ethylenically unsaturated. The term is thus to be understood as embracing, e.g., both dammar-3-ols and dammar-3-ones.

The term dammara compound as used herein is in particular to be understood as including 17C-dammara compounds, i.e. dammara compounds which are substituted at the 17-position by a group attached to the 17-position via a carbon atom. Such 17C-dammara compounds may be mono- or di-substituted, more conventionally mono-substituted, at the 17-position.

Preferred dammara compounds for use in accordance with the present invention are dammar-3-ols and physiologically hydrolysable and acceptable esters thereof and darnmar-3-ones and, in particular, 17C-dammara compounds. Especially preferred compounds for use in accordance with the invention are thus 17C-dammar-3-ols and physiologically hydrolysable and acceptable esters thereof and 17C-dammar-3-ones, for example compounds of formula IA

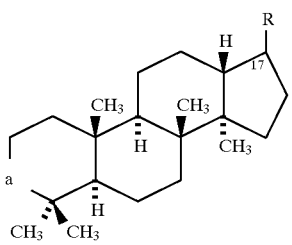

in which a is >CH—OR₁, in which $R_1$ is hydrogen or a physiologically cleavable and acceptable acyl residue, or >C=O and R is a group attached to the carbon atom at the 17-position by a carbon atom.

By the term "physiologically hydrolysable and acceptable ester" as used herein is meant any ester which is cleavable under physiological conditions to yield an acid which is itself physiologically tolerable at dosages to be administered. The term thus denotes pro-drug forms as known in the art, for example, acetates and the like. As applied to dammar-3-ols as defined above, the term denotes compounds in which the 3-hydroxy group is replaced by 3-acyloxy in which the acyl residue is physiologically cleavable and acceptable, that is cleavable under physiological conditions to yield the free dammar-3-ol and an acid which is physiologically tolerable at dosages to be administered. As will be appreciated, hydroxy groups present in dammara compounds at positions other than the 3-position may be similarly esterified, whereby such esters are also to be understood as embraced by the present invention.

17C-dammara compounds will generally comprise an asymmetric carbon atom at the 17-position. Such compounds will thus exist in diastereomeric form. In the case of, e.g. 17C-dammar-3-ols, a further asymmetric carbon atom is present at the 3-position, giving rise to further stereoisomeric variants. Where such isomers exist, the present invention is to be understood as embracing the use of both diastereomeric mixtures as well as of individual epimers. In general the use of dammara compounds in pure or substantially pure form, e.g. in the form of pure or substantially pure single epimers, e.g. comprising at least 90%, e.g. at least 95%, pure compound/epimer (i.e. containing 10% or less, preferably 5% or less, of other dammara compounds or epimeric contaminants) will be preferred. In the case of dammar-3-ols and their esters the hydroxy or ester, group at the 3-position will suitably have the β-configuration.

As previously indicated, various dammara compounds are known and described in the literature. In the case of known dammara compounds, the substituent at the 17-position is characteristically in the β-configuration. Dammara compounds in which the substituent at the 17-position is in the α-configuration are novel and are included per se within the scope of the invention. The 17α-dammara compounds advantageously exhibit better properties than the corresponding 17β-dammara compounds, for instance improved in vivo stability and enhanced biological activity, in particular in vivo.

Thus in a further aspect the present invention also provides:

b) A 17α-dammara compound, e.g. a 17αC-dammara compound: as well as:

c) A 17α-dammara compound, e.g. 17α-dammara compound, for use as set forth under a$^1$) above, for the preparation of a medicament as set forth under a$^2$) above or for use in a method of treatment as set forth under a$^3$) above.

Preferred 17α-dammara compounds in accordance with the invention are 17α-dammar-3-ols and physiologically hydrolysable and acceptable esters thereof and 17α-dammar-3-ones, e.g. 17αC-dammar-3-ols and physiologically hydrolysable and acceptable esters thereof and 17αC-dammar-3-ones.

Specific groups of 17α-dammara compounds in accordance with the present invention include:

17βH-dammara compounds (i.e. dammara compounds in which the 17α substituent is the sole substituent at the 17-position);

17 α,12βH-dammara compounds (i.e. dammara compounds in which any substituent at the 12-position is in the α configuration);

17 α,12 HH-dammara compounds (i.e. dammara compounds in which the 12-position is unsubstituted);

17α-dammara compounds which are substituted at the 17-position and, optionally, the 3-position only;

in particular any corresponding 17αC-dammara compound, -dammar-3-ol or physiologically hydrolysable and acceptable ester thereof, or -dammar-3-one, as well as any combination of such groups, for example 17αβH, 12βH-dammara compounds, -dammar-3-ols and so forth.

A particular group of 17α-dammara compounds in accordance with the present invention comprises the compounds of formula IB

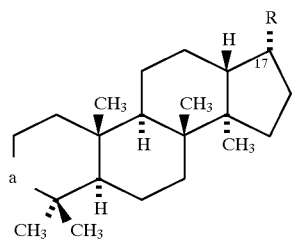

in which a and R have the meanings given for formula IA.

17C-substituents of 17C-dammara compounds for use in accordance with the invention as well as of 17αC-dammara compounds in accordance with the invention, e.g. groups R in formulae IA and IB are suitably hydrocarbyl groups, in particular aliphatic hydrocarbyl groups. Such aliphatic groups may be branched or straight chain, saturated or unsaturated and may bear one or more further substituents, in particular one or more hydroxy groups. Preferred aliphatic groups are unsubstituted or hydroxy-substituted aliphatic groups, in particular alkenyl or alkadienyl groups. Such aliphatic groups as aforesaid suitably comprise up to 8 carbon atoms. R is thus suitably a $C_8$-aliphatic group optionally comprising 1 or 2 double bonds and optionally substituted with at least 1 hydroxy group.

The present invention is to be understood as embracing both the individual epimers of 17α-dammara compounds as well as diastereomeric mixtures thereof, e.g. of 17α-dammar-3-ols. In general, e.g. for pharmaceutical use in accordance with the invention, 17α-dammara compounds in pure or substantially pure form (i.e. free or substantially free of 17β-dammara compound contaminants), e.g. comprising at least 90%, e.g. at least 95% 17α-dammara compound (i.e. comprising less than 10%, e.g. less than 5%, 17β-dammara compound contaminants), will be preferred. When the 17α-dammara compound itself exists in more than one epimeric form, use of pure or substantially pure single epimers, e.g. products comprising at least 90%, e.g. at least 95%, pure epimer, (e.g. comprising less than 10%, preferably less than 5% other epimeric contaminants) are preferred. In the case of 17α-dammar-ols and their esters, the hydroxy or ester group at the 3-position will suitably have the β-configuration.

The preferred compound of the invention is the compound of formula IC, ((17α)-23-(E)-dammara-20,23-dien-3β, 25-diol), in free or physiologically hydrolysable and acceptable ester form.

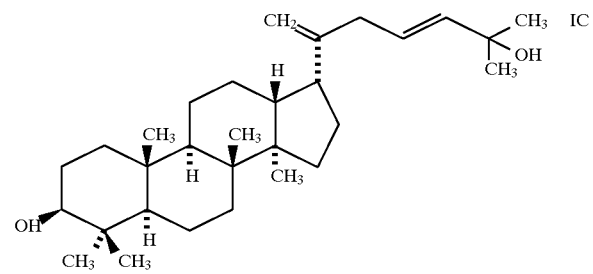

In accordance with the present invention, the novel compound of formula IC has been isolated from the flour of the shoots of the Palmyrah palm, *Borassus flabellifer* L. The Palmyrah palm is widely distributed in tropical regions of the Asian continent and constitutes a major ingredient of the daily diet in some countries. In Sri Lanka the outer portion of the young shoot, locally called Kottakilangu, is used either as a vegetable or dried and milled to provide a flour. This flour provides a convenient source for isolation of the compound of formula IC. The isolation and characterisation of the compound of formula IC are described in detail in Example 1.

Accordingly the invention also comprises a process for the preparation of a compound of formula IC which comprises isolating the compound from plant material, e.g. of the Palmyrah palm, *Borassus flabellifer* L.

Preferably the isolation process comprises extraction with an organic ester, e.g. ethyl acetate, followed by one or more chromatographic purification steps.

Many dammara compounds in which the substituent at the 17-position is in the β-configuration are known, e.g. the dammarenes, and may be obtained as natural products, e.g. as extracts from plant sources. For example many 17β-dammara compounds are obtainable from dammar resin (supplied by Fluka AG, CH-9470 Buchs, Switzerland) and other plant sources (see for instance the Dictionary of Steroids, Editors: Hill, Kirk, Makin & Murphy, published by Chapman & Hall, 1st Edition, 1991, pages 218–222 and 536). Dammara compounds may also be produced synthetically, for instance by suitable derivatisation and modification of naturally occurring dammarenes. Schemes, which are of general applicability for the synthesis of both 17α- and 17β-dammara compounds, are shown diagrammatically below.
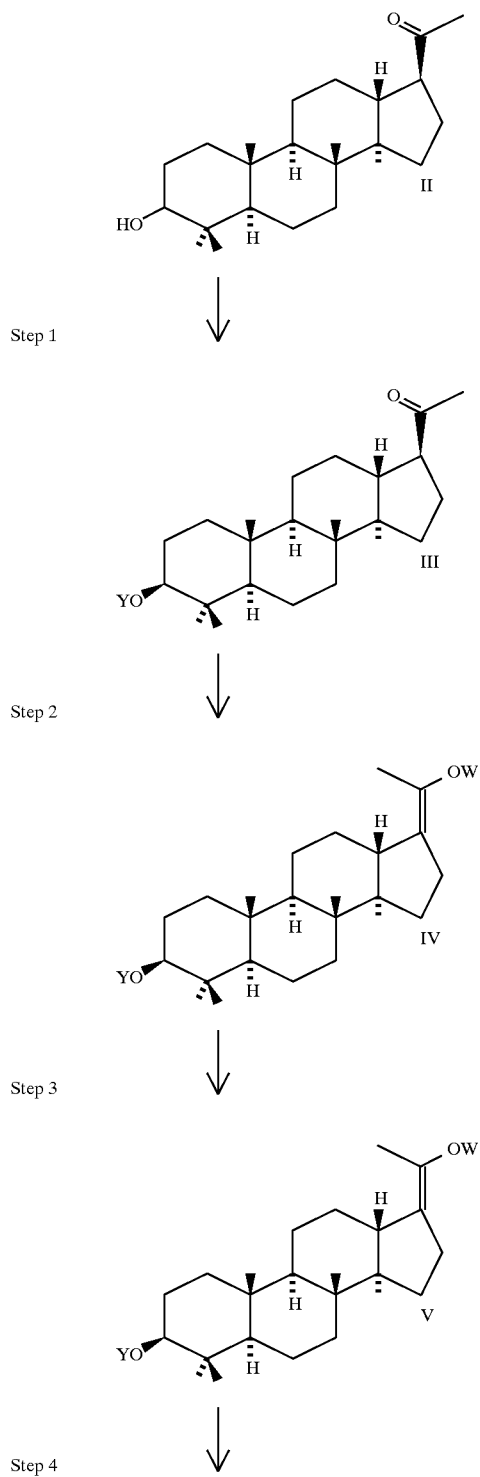
Scheme A

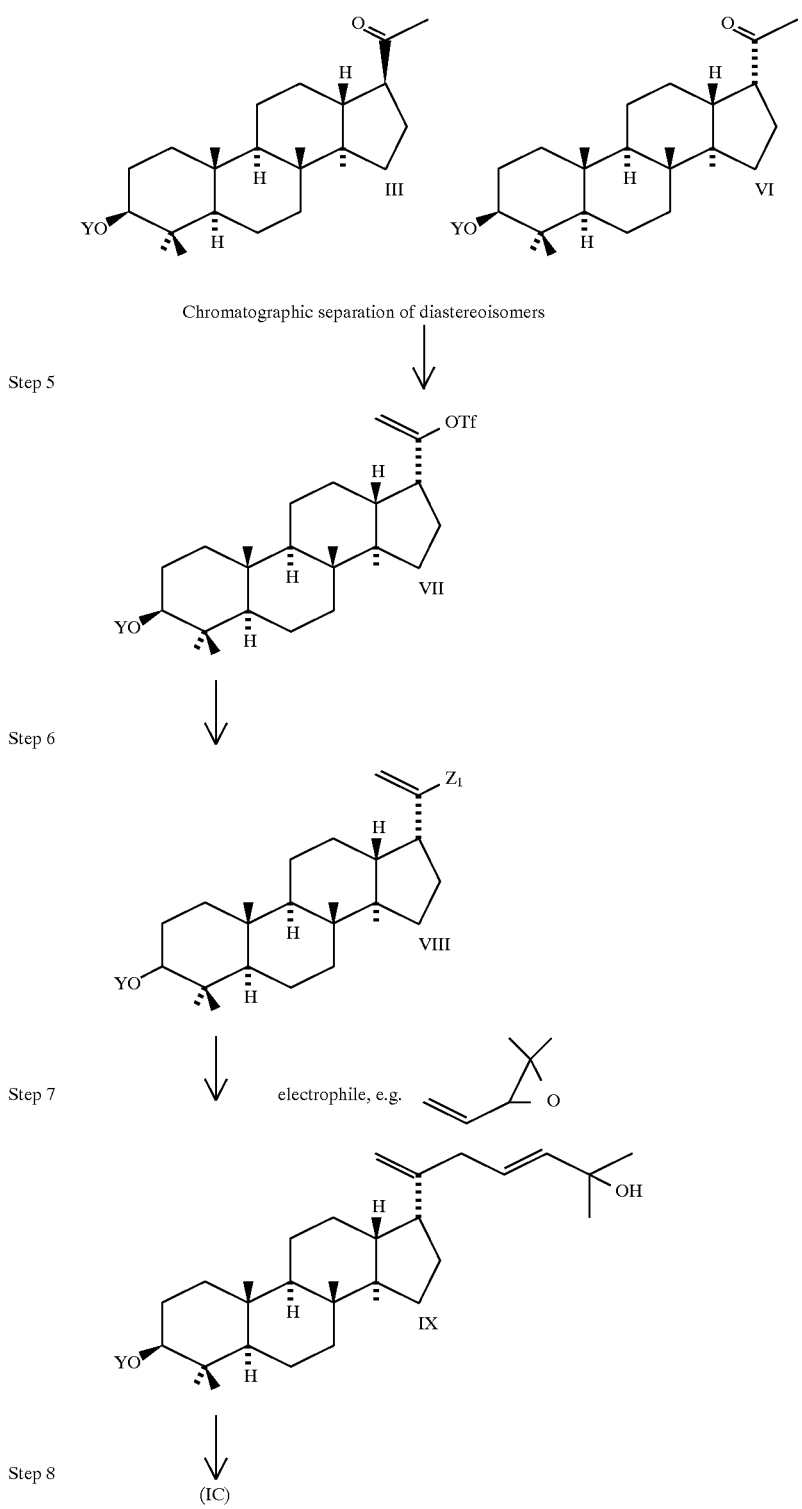

In the above scheme, steps 5 on are represented with respect to the 17α-epimer. These steps are of course equally applicable in respect of the 17β-epimer.

Step 1 comprises introduction of a hydroxy protecting group Y. Y may be any hydroxy protecting group which is compatible with, e.g. stable to, subsequent reaction steps. Suitably Y is a silyl hydroxy protecting group, e.g. tri($C_{1-4}$alkyl)silyl, for example t.-butyldimethylsilyl. Hydroxy protecting groups, Y, may be introduced by any of the means conventionally practised in the art, for example, by reaction of II with TBDMSC (t.-butyldimethylsilyl chloride) in imidazole.

Compound III is subjected to epimerisation via steps 2 through 4.

Step 2 comprises introduction of an acyl or silyl protecting group W. Suitable acyl or silyl protecting groups may be any of those known in the art which are susceptible to enol cleavage, e.g. employing a lithium organic compound or alkyl grignard reagent. Conveniently W is an acyl group, e.g. acetyl group, for example introduced by reaction of III with acetic anhydride in the presence of p-toluene sulphonic acid.

Step 3 comprises reaction of IV with a lithium organic compound. e.g. methyl lithium, or grignard reagent to provide a corresponding metal enolate, whereby M of V is appropriately magnesium or, preferably, lithium.

Step 4 comprises protonation of V to yield the diastereomeric mixture III+VI. Reaction may be carried out using any appropriate protonating agent, for example an alkyl ammonium chloride or methyl salicylate. As will be appreciated, by variation of parameters, e.g. choice of protonating agent and reaction conditions, step 4 may be varied to favour production of e.g. epimer VI.

Diastereomeric mixtures obtained from step 4 are suitably separated chromatographically following step 4 as indicated in scheme A.

Step 5 comprises triflation of VI, whereby Tf of VII is $CF_3$—$SO_2$—. Triflation is suitably performed, e.g. by reaction of VI with KHMDSA (potassium hexamethyldisylazane) and $PhNTf_2$ [N-phenyl-bis(trifluoromethanesulphonimide)].

Step 6 comprises reaction of VII with a metal organic sulfate, e.g. trialkyl tin cuprate, e.g. tributyl-tin cuprate, whereby Z of VII represents e.g. tributyl-tin. Tributyl-tin cuprate is suitably formed in situ, e.g. as hereinafter described in the accompanying example 2.

Step 7 comprises Stille coupling of VIII with an appropriate electrophile, e.g. in the presence of $Pd(CH_3CN)_2Cl_2$. In scheme A the electrophile is chosen to provide the specific end product of formula IC.

Step 8 comprises deprotection of IX to remove hydroxy protecting group Y. Deprotection may be performed by any of the means known and commonly employed in the art, for example, for the removal of silyl protecting groups by treatment with $Bu_4NF$ (tetrabutyl ammonium fluoride).

As will be appreciated by those skilled in the art, the above reaction scheme may be subject to adaptation, in particular to produce alternative 17α- and/or 17β-dammara compounds. Thus it will be appreciated that the precise nature of the substituent at the 17-position of the end product may be varied as desired by appropriate choice of electrophile used in step 7 or by subsequent modification of the initially obtained 17-position substituent. Further dammara compounds may be obtained, e.g. by modification of the 3-hydroxy group (e.g. to obtain corresponding keto compounds) or by choice of starting materials II in which e.g. the acetyl group at the 17-position is replaced by alternative acyl groups or reactive functional equivalents or in which the 3-position is oxo-substituted and, e.g. transforming the oxo group to a protected species, e.g. non-reactive functional equivalent, for the course of epimerisation and electrophilic substitution. Diastereomeric products may be separated, e.g. after completion of step 7 rather than 4, and 17β-epimers may be prepared starting from II and proceeding directly via steps 5 onwards.

In accordance with alternative scheme B shown below, products of step 4 of scheme A may be subjected to electrophilic substitution via Shapiro coupling procedure.

Scheme B

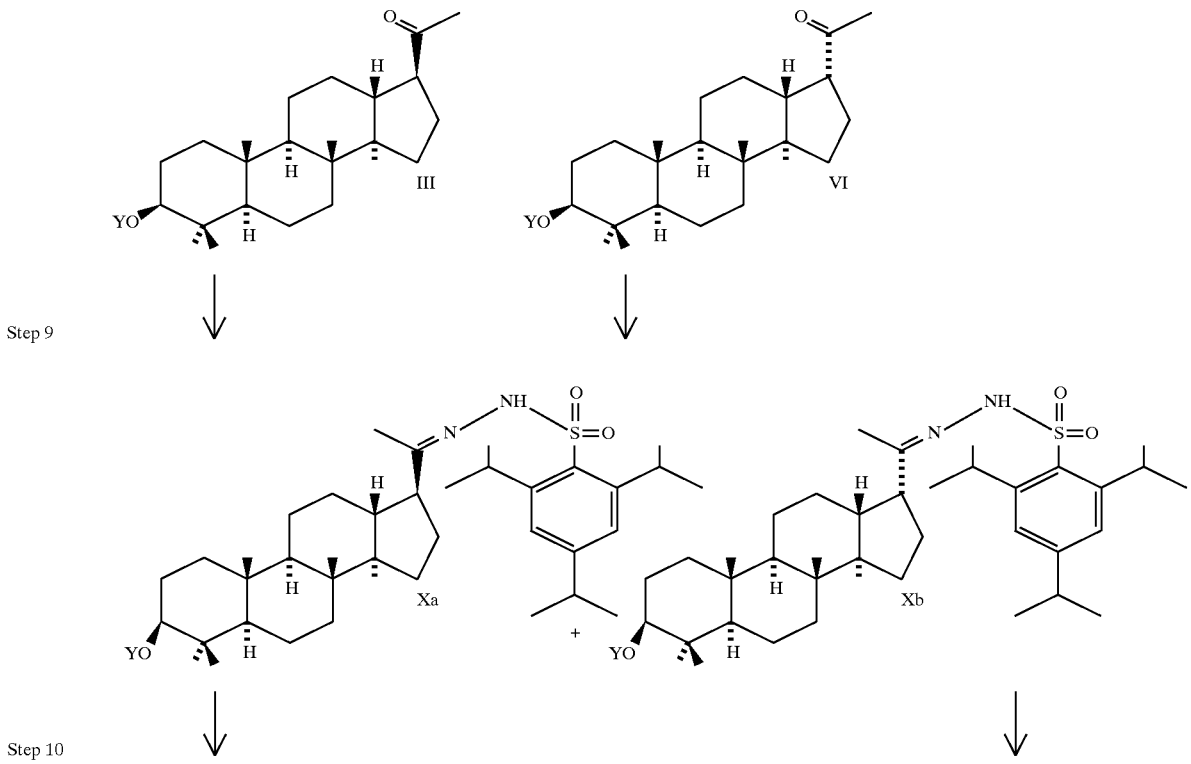

Step 9

Step 10

-continued
Scheme B

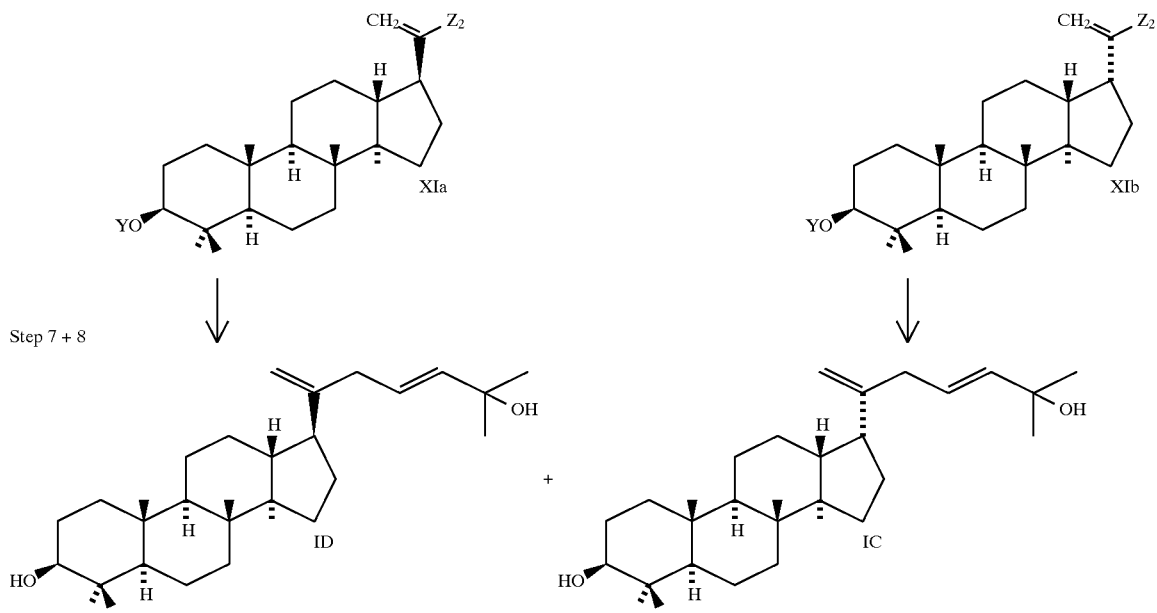

Step 9 comprises reaction of III or VI or mixtures thereof with trishydrazine hydrochloride. When the reaction is applied to 17α-dammara compounds and their synthesis, it is preferably performed under mild acidic conditions, e.g. in the presence of buffering agents. Step 9 is followed by reaction of Xa/Xb with an alkali metal organic compound, for example an alkyl lithium compound, e.g. butyl lithium, in step 10 to yield XIa/XIb in which $Z_2$ is an alkali metal, e.g. lithium, atom. XIa/XIb are processed further analogously to steps 7 and 8 hereinbefore described for reaction Scheme A, first, by reaction with CuCN to convert $Z_2$ to copper/alkali metal (e.g. copper/lithium) complex form followed by reaction with the chosen electrophile and deprotection.

Variation of the above process, e.g. as hereinbefore described in relation to Scheme A, is of course possible, in particular by use of alternative electrophiles. at step 10 leading to alternative substitution at the 17-position of the end product and by choice of alternative starting materials.

As will be appreciated from the foregoing, the present invention provides a novel process for the production of 17C-dammara compounds, including 17αC- as well as 17βC-dammara compounds, which, in broad application, comprises coupling of a 17carbonyl-dammara compound, e.g. 17acyl-dammara compound, in protected form as required, with an electrophile, e.g. an appropriate ethylenic peroxide, and, if desired, removing protecting groups or functionalities, for example coupling a compound of formula XII wherein, a" is >CH—OH or >C=0 in protected form and $R_2$ and $R_3$ are hydrocarbyl residues such that the sum of the number of carbon atoms in $R_2$ and $R_3$ is equal to the total number of carbon atoms in the desired substituent at the 17 position, removing the protecting group or functionality and, when required, acylating the obtained product with an appropriate acid to give a compound of formula IA as hereinbefore defined. Coupling may be carried out by any appropriate means though, by the procedures of reaction Schemes A and B, will proceed via a 17(organo-metal-C)-dammara compound (i.e. 17C-dammara compound in which the carbon atom of the 17C-substituent directly attached at the 17-position is substituted by an organo-metal group, e.g. a tri-alkyl tin group—cf. $Z_1$ of compound VIII, Scheme A) or 17(alkali metal-C)-dammara compound (i.e. 17C-dammara compound in which the carbon atom of the 17-substituent directly attached at the 17-position is substituted by an alkali metal, e.g. lithium, atom—cf. compounds XIa and XIb of Scheme B), for example a reactive intermediate of formula XIII

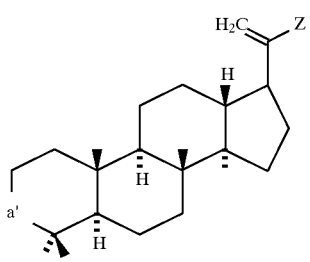

XIII wherein a' has the meaning given for formula XII and Z is an alkali metal atom or organo-metal group. Preferably Z is Li or tri-$C_{1-4}$alkyl-tin. The reactive intermediates may be prepared as such during a step in the coupling procedure or may be formed only transiently during the coupling procedure. 17β-carbonyl-dammara compounds, e.g. the compound of formula II, Scheme A are known [see e.g. Phytochemistry 26, (12), 3365 (1987) and Tetrahedron 29, 2105 (1973)] or may be prepared analogously to the known compounds or by derivatisation thereof. 17α-carbonyl-dammara compounds, e.g. compounds of formula IV, Scheme A are new.

As will be further appreciated, the present invention also provides a process for the production of 17α-carbonyl-dammara compounds which process comprises epimerising a corresponding 17β-carbonyl-dammara compound in protected form as required and, if desired removing protecting groups or functionalities, for example epimerising a compound of formula XIIa

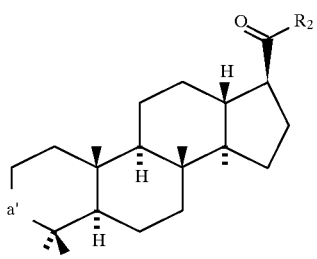

XIIa wherein a' and $R_2$ have the meanings given for formula XII, and, if desired, removing the protecting group or functionality, to produce a compound of formula XIIb

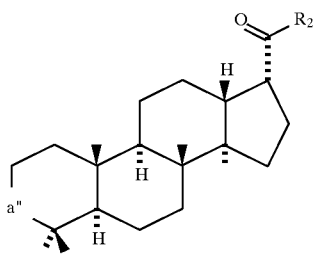

XIIb wherein a" is >CH—OH or >C=O in free or protected form and $R_2$ has the meaning given for formula XII. Specific procedures for effecting epimerisation are as hereinbefore described in relation to steps 1 to 4 of Scheme A, with optional deprotection in accordance with the general procedures of step 8.

As already noted, 17α-carbonyl-dammara compounds, e.g. of formulae XIIb and VI are new. 17αC-dammara compounds wherein the substituent at the 17-position is as represented in each of formulae IV, V, VII to IX, Xa/b and XIa/b are also new. They are useful as intermediates and are also to be understood as being within the scope of the present invention. Of these compounds the 17α-carbonyl-dammara compounds are of special interest, in particular as intermediates.

Accordingly, in a further and specific aspect the present invention provides:

d) a 17α-carbonyl-dammara compound.

Preferred dammara compounds d) are 17α-acyl-dammara compounds, e.g. compounds of formula XIIb, for example 17α-acetyl-dammara compounds, e.g. as represented by compounds of formula VI.

17(organo-metal-C)- and 17(alkali metal-C)-dammara compounds, including both 17β- and, especially, 17α-(organo-metal-C)- and -(alkali metal-C)-dammara compounds, are also of special interest, in particular as intermediates.

Accordingly, in a yet further and specific aspect, the present invention provides: e) a 17(organo-metal-C)- or 17(alkali metal-C)-dammara compound.

Preferred compounds e) are 17(1-organo-metal-vinylene)- and 17(1-alkali metal-vinylene)-dammara compounds as exemplified, e.g. by formula XIII, for example 17(1-organo-metal-vynyl)- and 17(1-alkali metal-vinyl)-dammara compounds as exemplified, e.g. by formulae VIII, XIa and XIb.

Suitable organo-metal groups and alkali metal atoms are as hereinbefore described, whereby 17(lithium-C)-, for example 17(1-lithium-vinylene)-, e.g. 17(1-lithium-vinyl)-dammara compounds are of particular interest.

Having regard to the superiority of end products obtainable from them, 17α-dammara compounds as defined under e) are preferred.

Particular groups of 17α-carbonyl-, 17(organo-metal-C)- and 17(alkali metal-C)-dammara compounds d) and e) within the ambit of the present invention include any of those hereinbefore defined in relation to 17α-dammara compounds generally, including, e.g. 17α-carbonyl-, 17-(organo-metal-C)- and 17(alkali metal-C)- -dammar-3-ols and -dammar-3-ones, each in free or protected form, as well as 17α-carbonyl,βH and 17α,12βH-dammara compounds and so forth.

As will be appreciated from the process description hereinabove, 17(organo-metal-C)-dammara compounds may be prepared, e.g. by triflating a 17carbonyl-dammara compound, to obtain a 17(trifluoromethylsuphate-C)-dammara compound and reacting this with a metal organic cuprate, whereby the starting material is protected as appropriate, the procedure being followed by optional deprotection, e.g. removal of protecting groups or functionalities, for example, triflating (e.g. as hereinbefore described for step 5, reaction Scheme A) a compound of formula XII as hereinbefore defined, for example wherein $R_2$—CO—represents an acyl, e.g. $C_{1-4}$acyl, e.g. acetyl, group, and reacting the obtained product with an alkali metal organic compound (e.g. as hereinbefore described for step 6, reaction Scheme A) and, optionally deprotecting the product, e.g. removing protecting groups or functionalities, to obtain a compound of formula XIIIa.

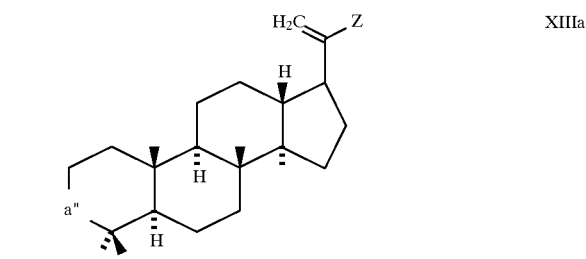

XIIIa wherein a" has the meaning given for formula XIIb and Z is an organo metal group, e.g. trialkyl tin, e.g. tributyl tin group.

17(Alkali metal-C)-dammara compounds may be prepared by reacting a 17-carbonyl-dammara compound with trishydrazine HCl and reacting the obtained product with an alkali-metal organic compound, for example butyl lithium, whereby the starting material is protected as appropriate, the procedure being followed by optional deprotection, e.g. removal of protecting groups or functionalities, for example, reacting a compound of formula XII as hereinbefore defined, for example wherein $R_2$—CO— represents an acyl, e.g. $C_{1-4}$acyl, e.g. acetyl, group with trishydrazine HCl and reacting the obtained product with an alkali metal organic compound, for example, as described above and, optionally, deprotecting the product, e.g. removing protecting groups or functionalities, to obtain a compound of formula XIIIa as illustrated above, wherein a" has the meaning given for formula XIIb and Z is an alkali metal, e.g. lithium, atom.

As will be appreciated dammara compounds for pharmaceutical use in accordance with the invention will in particular be physiologically tolerable or pharmaceutically acceptable, e.g. non- or substantially non-toxic at dosages to be administered or having a level of toxicity which is acceptable at dosages to be administered, e.g. having regard to the disease or condition to be treated. Choice of appropriate dammara compounds for pharmaceutical use may be effected by application of technologies known and commonly applied in the pharmaceutical arts.

Dammara compounds, in particular 17α-dammar compounds as hereinbefore set forth, e.g. a compound of formula I, IA, IB or IC, possesss pharmaceutical utility as demonstrated in the following test methods.

1. Proliferative Response Of Lymphocytes to Allogenic Stimulation

Two-way MLR (Murine Mixed Lymphocyte Reaction)

Spleen cells (0.5×106) from Balb/c mice (female, 8–10 weeks) are co-incubated for 5 §days with 0.5×10$^6$ spleen cells from CBA mice (female, 8–10 weeks). The allogenic cells induce a proliferative response in the responder spleen cell population which is measured by labelled precursor incorporation into the DNA. Test compounds are added at the start of incubation at varying concentrations and proliferative response compared with untreated controls. Dammara compounds typically have an $IC_{50}$ from about 100 to about 10 nM or lower (as compared to an $IC_{50}$ of about 2 nM for cyclosporin A) in this assay.

Reference

T. Meo (1979) The MLR in the mouse. In: "Immunological Methods", L. Lefkovits and B. Pernis, Eds., Academic Press, N.Y. pp. 227–239

2. Cytotoxic and cytostatic activity using a transformed human T-cell line (Jurkat)

5×10$^4$ Jurkat cells are grown in a final volume of 0.2 ml for 72 hours after which the cell numbers are enumerated by use of an enzymatic assay using p-nitrophenyl-N-acetyl-β-D-glucosamindle as substrate. Test compounds are added at varying concentration at the start of culture and cytotoxicity compared with untreated controls. Dammara compounds are found inactive at concentrations of up to 5μM, indicating that immunosuppressive activity is specific.

3. Cytotoxic and cytostatic activity in vitro using the P-815 mastocytoma cell line A Costar 96-well plate is filled with medium (100 μl/well), the compounds to be tested are added to the top row in 25 μl aliquots, mixed, 25 μl aliquots are removed from each well and added to the corresponding well in the next lower row. Medium addition, mixing and transfer of 25 μl to the next lower layer is repeated until the end of the plate is reached. The last 25 μl are discarded. 100 μl of cell suspension (P-815 mastocytoma cells, 30 000 cells/well) is then added to each well and incubation carried out for 48 hours at 37° C. in a humidified atmosphere of air +5–7% $CO_2$. Cell proliferation is assessed by use of a cell counter or by an enzymatic-colorimetric assay: plates are centrifuged for 10 minutes at 3000 rpm (EC Centra-7R). Supernatant is discarded carefully, the cells washed once with PBS (Dulbecco, without calcium and magnesium) and 50 μl/well of a 0.5% Triton-X 100 solution (0.5 ml Triton X-100 in 99.5 ml water) is added and the plates shaken well for 5–10 minutes at room temperature. Substrate (p-nitrophenyl-N-acetyl-β-D- glucosaminide, 50 μl/well) is added before incubation for 60 minutes at 37° C. 150 μl of buffer 2 is then added and the plates read at 405 nrn. Test compounds are added at the start of incubation at varying concentration and cell proliferation compared with untreated controls. Dammara compounds are found not to influence proliferation at concentrations of up to 5 μM, indicating that immunosuppressive activity is specific.

Reference

H. Staehelin (1962) A simple quantitative test for cytostatic agents using non-adhering cells in vitro. Med. exp. 7:92–102

4. Localised Graft-versus-Host (GvH) Reaction in the rat [Ford et al., TRANSPL. PROC. 10 (1979) 258].

Spleen cells (1×10$^7$) from 6 week old female Wistar/Furth (WE) rats are injected subcutaneously on day 0 into the left hind-paw of female (F344×WF)$F_1$ rats weighing about 100 g. Animals are treated for 4 consecutive days and the popliteal lymph nodes are removed and weighed on day 7. The difference in weight between the two lymph nodes is taken as the parameter for evaluating the reaction. Test compounds are administered daily for 4 days at varying dosage p.o. and inhibition compared with untreated controls. Dammara compounds are active (inhibit GvH reaction) in this test model at doses of the order of from 10 μg to 10 mg/kg/day p.o.. 17α-dammara compounds (e.g. the compound of formula IC) are found to be up to about 100× more active than corresponding 17β-epimers.

5. Kidney Allograft Reaction in the Rat

One kidney from a female Fisher 344 rat is transplanted onto the renal vessel of a unilaterally (left side) nephrectomised WF recipient rat using an end-to-end anastomosis. Urethric anastomosis is also end-to-end. Treatment with test compound at varying dosages p.o. commences on the day of transplantation and is continued for 14 days. A contralateral nephrectomy is done seven days after transplantation, leaving the recipient relying on the performance of the donor kidney. Survival of the graft as compared with control is taken as the parameter for a functional graft. Dammara compounds prolong graft survival in this test model at doses of the order of from 10 μg to 10 mg/kg/day p.o.. 17μ-dammara compounds are found to be substantially more potent (up to ca. 100 to 1000×) than 17β-dammara compounds.

6. Experimentally Induced Allergic Encephalomvelitis (EAE) in the Rat

[Levine et al., AM. J. PATH. 47 (1965) 61; McFarlin et al, J. IMMUNOL. 113 (1974) 712; Borel, TRANSPLANT & CLIN. IMMUNOL. 13 (1981) 3].

Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded. Test compound is administered p.o. at varying dosage for 12 days starting at sensitisation. Dammara compounds inhibit disease onset in this test model at doses of the order of from 10 μg to 10 mg/kg/day p.o.. 17α-dammara compounds are found to be substantially more potent (ca. 100 to 1000×) than 17β-dammara compounds.

7. Freund's Adjuvant-induced Arthritis

[Winter & Nuss, ARTHRMS AND RHEUMATISM 9 (1966) 394; Billingham & Davies, HANDBOOK OF EXPERIMENTAL PHARMACOL (Vane & Ferreira Eds, Springer Verlag, Berlin,) 50/II,(1979) 108–144]

OFA and Wistar rats (male or female, 150 g body weight) are injected i.c. at the base of the tail or in the hind paw with 0.1 ml of mineral oil containing 0.6 mg of lyophilised heat-killed Mycobacterium smegmatis. In the developing arthritis model, treatment with test compound is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. Dammara compounds inhibit disease progression in the developing or established test models at daily doses of the order of 10 μg to 10 mg/kg. 17α-dammara compounds are found to be substantially more potent than 17β-dammara compounds.

8. Primary Humoral Immune Response to Sheep Red Blood Cells (MD, Mishell-Dutton)

Mouse spleen cells (OF 1, female, 8–10 weeks, 1×10$^7$) are co-cultured with sheep erythrocytes (SRBC, 3×10$^7$) for 3 days in 1 ml final volume in 24 well plates. Lymphocytes are harvested, washed and plated at a density of 1×10$^6$ cells onto soft-agar with fresh antigen (SRBC). Complement (guinea pig serum) is added after a 60–90 minute incubation period and incubation is continued for another 60 minutes after which the test is evaluated by counting (microscope) the plaques. During the 3 day incubation, the lymphocytes are sensitized to the antigen (SRBC). When incubated with antigen again, B-lymphocytes secrete specific antibody which binds to the antigen in the vicinity of the secretory lymphocyte. Addition of complement causes lysis of the antibody-coated erythrocytes yielding a plaque. Each plaque represents a single antibody-producing cell. Test compound is added at the start of incubation at varying concentration. Dammara compounds inhibit plaque formation in this test model at concentrations of the order of from 10 to 100 nM.

References

R. I. Mishell & R. W. Dutton (1966) Immunization of normal mouse spleen cell suspensions in vitro. Science 153: 1004–1006; and R. I. Mishell & R. W. Dutton (1967) Immunization of dissociated spleen cell cultures from normal mice. J.Exp.Med. 126:423–442.

9. DTH (relayed-type hypensensitivity) induced by SRBC-T$_H$ cells

Fifty microliters of a 1:1 (v/v) mixture of a T$_H$ (sheep red blood cell primed) cell clone (2×10$^6$) and a 10% sheep red blood cell (SRBC) suspension are injected s.c. into the right hind footpad of female C57 BL/6 mice (6–12 weeks old). 50 μl of the SRBC cell suspension (diluted 1:1 v/v with PBS) is injected s.c. into the left hind footpad (to measure non specific increase in footpad swelling due to the injection procedure). Right and left hind footpad thickness is measured 24 hours later. Test compounds are administered 24 hrs. and 2 hrs. prior to challenge at varying dose p.o.. At the end of the experiment, the percent increase in thickness of the right footpad over the left footpad is calculated. [Thickness of right footpad =x; thickness of left footpad=y; % specific increase=z: z=((x-y)/y).100]. 17α-dammara compounds inhibit DTH reaction in this test model at doses of the order of 1 to 100 μg/kg p.o.. 17β-dammara compounds inhibit DTH reaction at doses of the order of 1 to 100 mg/kg.

References

A. T. J. Bianchi, H. Hooijkaas, R. Brenner, R. Tees, A A. Nordin & M. H. Schreier (1981) Clones of helper T-cells mediate antigen specific, H-2 restricted DTH. Nature 290:62–63; and P. Herrmann, M. H. Schreier, J.-F. Borel & C. Feurer (1988) Mast cell degranulation as a major event in the effector phase of delayed-type hypersensitivity induced by cloned helper T cells. Int. Archs Allergy appl. Immun. 86: 102–105.

10. Systemic lupus erythematosus (SLE) in the mouse (NZB/NZW)

Female New Zealand black/white (NZB/NZW) F1 mice spontaneously develop characteristics that resemble systemic lupus erythematosus. At 2 to 3 months they develop antinuclear antibodies, at 5 to 6 months they develop systemic immune nephritis and proteinurea, and have a predictable course to chronic renal mortality rate at 8–9 months of age. Treatment starts at 24 weeks of age when animals show proteinurea. Compounds are administered p.o. 3 times a week for a total of 12 weeks. Status is determined every second week and animals are sent for histological evaluation at termination of the experiment Ten mice are used per group. 17α-dammara compounds are active in preventing disease onset in the above test model on administration every 2 days at doses of 5 to 100 μg/kg p.o.. 17β-dammara compounds are similarly active on administration every 2 days at doses of 1 to 100 mg/kg p.o..

Reference

B. S. Andrews, R. A. Eisenberg, A. N. Theofilopoulos, S. Izui, C. B. Wilson, P. J. Mc J. B. Roth & F. J. Dixon (1978) Spontaneous murine lupus-like syndroms: clinical a manifestation in several strains. J.Exp.Med. 148:1198.

Dammara compounds, e.g. 17α-dammara compounds, as hereinbefore described, e.g. a compound of formula I, IA, IB or IC, are accordingly useful as a pharmaceuticals, e.g. as immuno-suppressive as well as antiinflammatory agents.

As immunosuppressive agents they are, in particular, useful for the prevention of acute and/or chronic organ or tissue transplant rejection, e.g. for the treatment of recipients of heart, lung, combined heart-lung, liver, kidney, pancreatic, skin or corneal transplants. They are also indicated for the prevention of graft-versus-host disease, such as following bone marrow transplants.

As immunosuppressive and antiinflammatory agents they are also useful for the treatment of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which dammara compounds may be employed include autoimmune haematological disorders (including e.g. haemolytic anaemia, aplastic anaemia, pure red cell anaemia and idiopathic thrombocytopenia), systemic lupus erythematosus, polychondritis, scierodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Dammara compounds, e.g. 17α-dammara compounds, as hereinbefore described are further indicated for use in the treatment of alopecia/the promotion of hair growth and for the treatment of asthma, e.g. on administration by inhalation.

Dammara compounds, e.g. a 17α-dammara compounds as hereinbefore described, are also indicated for use in conditions in which corticosteroids may be used.

For the above indications the appropriate dosage will, of course, vary depending, for example, on the subject to be treated, the mode of administration and the nature and severity of the condition being treated and the effect desired. However, in general, satisfactory results in animals are obtained at daily dosages of from about 0.001 to 10 mg/kg/day p.o.. In larger mammals, for example humans, an indicated daily dosage is in the range of from about 0.05 to about 500 mg of the compound administered orally once or, more suitably, in divided dosages two to four times/day whereby doses required for 17α-dammara compounds will be at the upper end of this range and doses for 17β-dammara compounds will be at the lower end.

In organ transplantation in humans an indicated dosage regimen comprises an initial single oral dose of 0.05–10 mg/kg of the compound, 4–12 hours prior to surgery and maintained as daily dose for one to two weeks post-operatively, before being gradually reduced in accordance with blood levels until a maintenance dose of about 0.02–2 mg/kg/day is reached. When the compound is given along with other immunosuppressants, e.g. as part of a triple or quadruple drug therapy, lower doses (e.g. 0.01 mg/kg/day i.v.; 0.01–1 mg/kg/day oral initially) may be used.

Dammara compounds, e.g. 17α-dammara compounds, as hereinbefore described may be administered by any conventional route, in particular enterally, e.g. orally, for example in the form of solutions for drinking, tablets or capsules or parenterally, for example in the form of injectable solutions or suspensions. Normally for systemic administration oral dosage forms are preferred, although for some conditions, for example for prevention of rejection of liver transplants, an intravenously injectable form is desirable. The compound may also be administered topically or dermally, e.g. in the form of a dermal cream or gel or like preparation or, for the purposes of application to the eye, in the form of an occular cream, gel or eye-drop preparation. Suitable unit dosage forms for oral administration comprise e.g. from 0.05 to 10 mg or 12.5 mg of the compound per dosage.

Pharmaceutical compositions for administration of dammara compounds, e.g. 17α-dammara compounds, as hereinbefore described may be prepared by any means known or conventionally employed in the galenic art, e.g. by intimate admixture with appropriate pharmaceutically acceptable diluents or carriers including pharmaceutical or injectible grade water. As previously indicated pharmaceutical compositions comprising dammara compounds, e.g. a 17α-dammara compound will appropriately comprise a dammara compound in pure or substantially pure form, e.g. in the form of a pure on substantially pure single epimer.

In accordance with the foregoing the present invention also provides:

f) A pharmaceutical composition comprising a dammara compound, e.g. a 17α-dammara compound, as herein-before described, e.g. a compound of formula I, IA, IB or IC, in combination with a pharmaceutically acceptable diluent or carrier.

Figure 2:
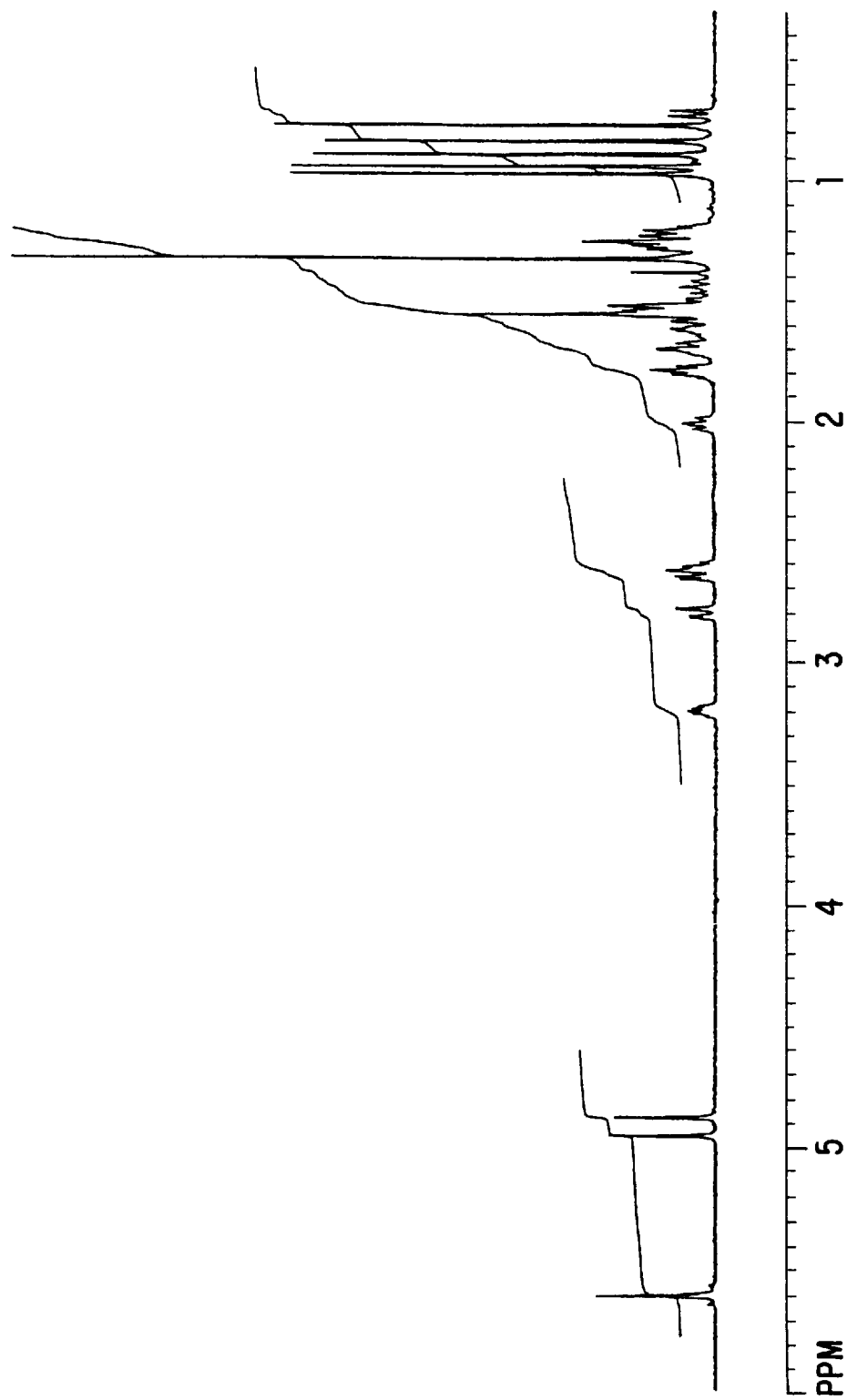
Figure 3:
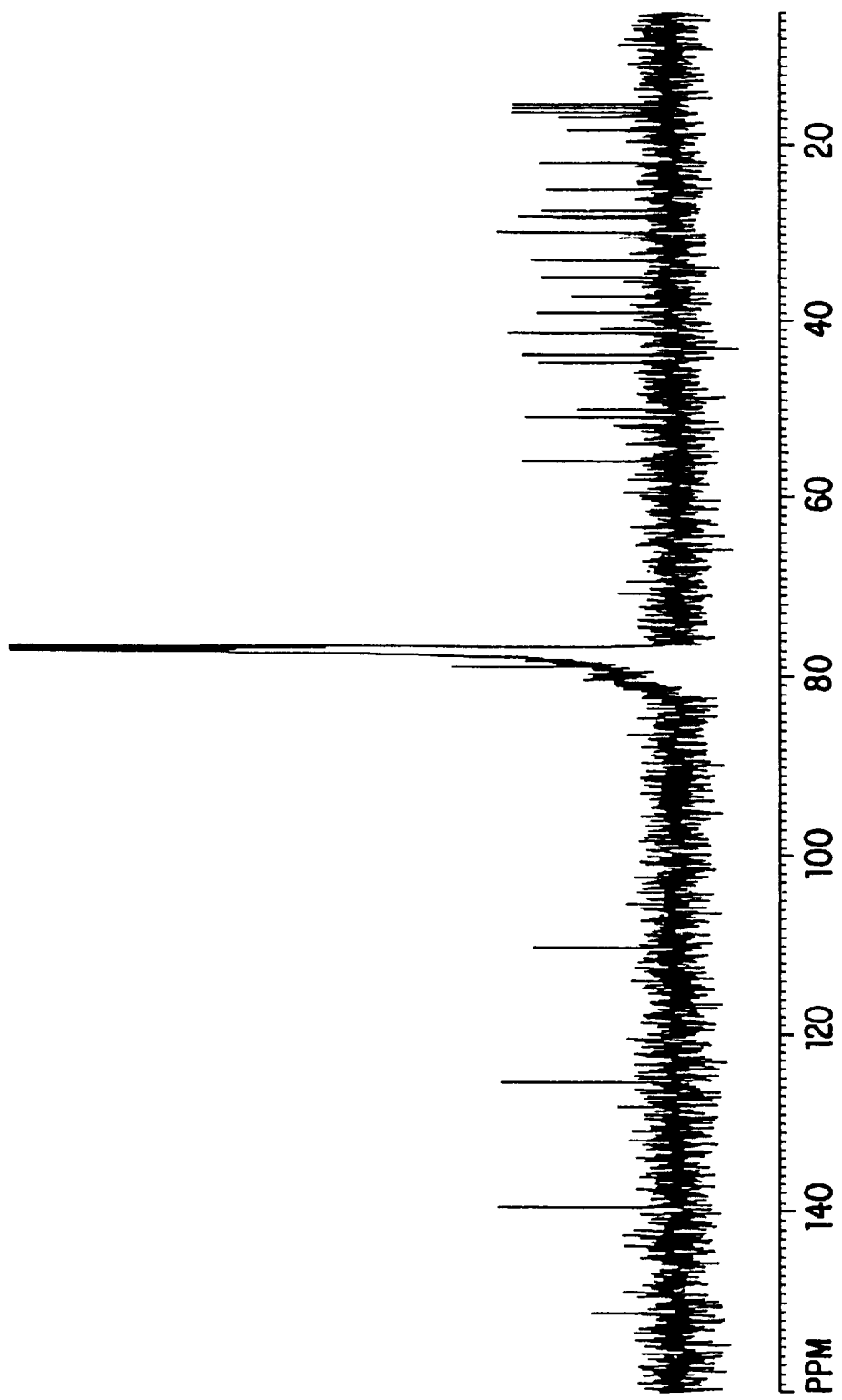

The invention is further described by way of illustration only in the following Example which refers to the accompanying Figures: in which FIG. 1 is a graph showing the results of a delayed type hypersensitivity (DTH) test conducted on samples of Palmyrah flour extract and control samples; FIG. 2 is the proton NMR spectrum of the compound isolated in the Example 1, and FIG. 3 is the $^{13}$C-NMR spectrum of the compound isolated in the Example 1.

EXAMPLES

Example 1

Isolation and characterisation of the compound of formula IC

Preliminary Studies 4 aliquots of Palmyrah shoot flour (*Borassus flabellifer* L.) 10 g each are extracted with 200 ml of the following solvents to identify a suitable extraction procedure.

ethyl acetate (A)

petrol ether (B)

methanol (C)

water (D)

1 aliquot of 600 g is extracted using a soxhlet and hexane (boiling point 60°–70° C.) for 16 hours, followed by boiling dichloromethane for 16 hours. This procedure yields after evaporation in vacuo 1.1639 g of hexane extract (E) and 0.335 g of dichloromethane extract (F).

Fractions are dissolved in ethanol and tested in the Mishell-Dutton assay (primary humoral immune-response to SRBC in vitro, MD) a mixed lymphocyte reaction (MLR) and on the P-815 mastocytoma cell line for cytotoxicity.

Results with exploratory extracts

Extracts A, B, and E show inhibitory activity on activated lymphocytes in vitro (MD test 8 hereinbefore) with extract A) being the most active ($IC_{50}$ approx. at a conc. of less than 1:4000 dilution). The least active of the active fractions is extract E ($IC_{50}$ of about 1:200 dilution). The least toxic in the P-815 mastocytoma (test 3 hereinbefore) is Extract B. However, the best activity to toxicity ratio is found in Extract A), being the most active in inhibiting the mixed lymphocyte reaction (test 1 hereinbefore). The results obtained are given below in Tables 1, 2 and 3.

TABLE 1

| Primary humoral immune response (MD) | | |
|---|---|---|
| Extract | Concentration | % Inhibition |
| A | 1:40 | 100 |
|   | 1:400 | 100 |
|   | 1:4000 | 76 |
| B | 1:40 | 100 |
|   | 1:400 | 90 |
|   | 1:4000 | 52 |
| E | 1:40 | 100 |
|   | 1:400 | 20 |
|   | 1:4000 | 5 |

TABLE 2

Mixed lymphocyte reaction

| Extract | Concentration | % Inhibition |
|---|---|---|
| A | 1:500 | 100 |
|   | 1:2500 | 70 |
|   | 1:12500 | −50 stimulation |
| B | 1:500 | 100 |
|   | 1:2500 | −40 |
|   | 1:12500 | −42 |
| E | 1:500 | −40 |
|   | 1:2500 | −30 |
|   | 1:12500 | −29 |

TABLE 3

P-815 mastocytoma (cytotoxicity assay)

| Extract | Concentration | % Inhibition |
|---|---|---|
| A | 1:50 | 100 |
|   | 1:250 | 100 |
|   | 1:1250 | 38 |
| B | 1:50 | 100 |
|   | 1:250 | 90 |
|   | 1:1250 | −2 |
| E | 1:50 | 100 |
|   | 1:250 | 65 |
|   | 1:1250 | 10 |

The various extracts are also assessed the in vivo delayed-type hypersensitivity reaction (test 9 hereinbefore), to obtain additional information for the decision as to which extracts should be used for large scale extraction. For this purpose equal aliquots (extracts from 10 g flour) are given orally once to five mice one hour prior to the antigen administration. The reaction is read 24 hours after antigen injection. Cyclosporin A is used as a positive control. The results are given in FIG. 1. Only extract A/B (extracts A and B in combination) shows appreciable inhibitory activity in vivo.

Extract A (ethyl acetate) showes the most promising effects in vitro and in vivo and is chosen for large scale extraction.

Isolation and Characterisation of the compound of formula IC 50 kg Palmyrah flour (*Borassus flabellifer* L.) is divided into 5×10 kg portions, each extracted with 20 l ethyl acetate at room temperature and filtered after 1 hr. This procedure is repeated with 15 l ethyl acetate. The combined filtrates (175 l) are concentrated in vacuo to a brown oily residue of 95.5 g, which is then partitioned 3× in the solvent system 90% aqueous methanol (500 ml) and hexane (1 l), the lower phase giving 19.8 g of a crude solid after evaporation in vacuo. This is applied to a 8×35 cm column containing approximately 2 kg silica gel 60, and chromatographed with a mixture of methyl-tert butylether/methanol, the content of methanol being increased stepwise from 2% to 50%. Three (3) fractions No. 1, 2 and 3 (each of 450 ml) with activity mainly in the MLR test are collected.

Fractions No. 2 and 3 (1.92 g) are further applied to a 5.5×36 cm silica gel column, which is eluted with a mixture of hexane/acetone, the content of the latter being increased stepwise from 20% to 50%. 22 fractions (1.19 g) from this column identified by TLC and bio-activity are combined with the remaining MLR active fraction No. 1 (0.28 g) from the preceding chromatography step. The next purification step is performed on a Sephadex LH-20 column (5×85 cm) with dichloromethane/methanol (1:1) elution and UV monitoring at 220 nm, giving 6 bio-active fractions which yield 809 mg of product. This product is further processed in 3 equal runs with preparatory HPLC on a 20×250 mm column of Spherisorb ODS-2 RP18 (5 μm). A linear (70%→100%) gradient of acetonitrile/methyl-tert.butyl-ether (9:1) in water is applied and fractions are recovered using UV monitoring at 220 nm.

6 MLR active fractions (32 mg) are collected and separated on the same HPLC column as above, though eluting with an isocratic mixture of methanol/water/methyl-tert.butyl-ether (7:2:1) and detecting at 220 nm, giving 7 active fractions totaling 9.3 mg. This step is repeated on the same HPLC column with isocratic acetonitrile/water (87:13) elution and monitoring at 220 nm. Four (4) active fractions (1.3 mg) are detected. A 100 μg aliquot is finally separated on a 4×250 mm HPLC column of LiChrospher RP18 (5 μm) with acetonitrile elution of 1.5 ml/min. Fractions are taken based on diode array UV detection, simultaneously at 220 and 240 nm. MLR activity is shown to be present in a fraction with a single and pure HPLC peak at several wavelengths and with a retention time of approx. 11.6 min. Remaining activity (1.1 mg) from the preceding step is processed in 11 aliquots of 100 μg in exactly the same way, and the fractions with the single pure peak gave, after collection and concentration, 0.5 mg of a white amorphous compound. The properties and physical characteristics of this compound are set out in Table 4 below.

The activity of the isolated compound in the murine mixed lymphocyte reaction (MLR), test 1, and the Jurkat and P-815 cytotoxic/cytostatic activity, test 3, is measured and compared with the activities of cyclosporin A and silicicolin in the same assays. The results obtained are given in Table 5 below.

TABLE 4

Properties

| | |
|---|---|
| 1. Appearance | colorless powder |
| 2. Mass spectrum (FAB) | m/e = 443 (MH$^+$) |
| 3. Molecular formula | $C_{30}H_{50}O_2$ |
| 4. UV spectrum (MeOH) | End absorption |
| 5. Proton NMR, 500 MHz in CHCl$_3$ as int. stand. | CDCl$_3$, see FIG. 2 |
| 6. $^{13}$C-NMR, 125.7 MHz, CDCl$_3$ as int. stand. | in CDCl$_3$, see FIG. 3 |
| 7. Solubility | soluble in chloroform and methanol, insoluble in water |
| 8. HPLC[a] (Rt) | 11.6 minutes |

[a]Merck LiChrospher 100 RP-18 (5 μm), 4 × 250 mm; acetonitrile at 1.5 ml/min.; detection at 210 nm using a Waters 996 photodiode array detector

TABLE 5

Biological activities of the isolated compound in vitro, as compared with Cyclosporin A and Silicicolin
IC$_{50}$ (ng/ml)

| | MLR | Jurkat | P-815 |
|---|---|---|---|
| Cyclosporin A | 4 | >5000 | >5000 |
| Silicicolin | 2 | 2.5 | 4 |
| Formula IC comp. | 10.5 and 11.0 | >5000 | >5000 |

Cyclosporin A is employed as a reference immunosuppressive agent.
Silicicolin is employed as a reference cytostatic agent.

EXAMPLE 2

Synthesis of (17α)-23-(E)-dammara-20,23-diene-3β,25-diol (COMPOUND OF FORMULA IC)

a) Process step 1, Scheme A

3β-t.-Butyl-dimethylsiloxy-17α-acetyl-hexanor-dammarane

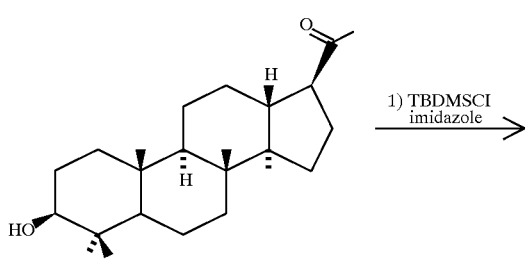

A

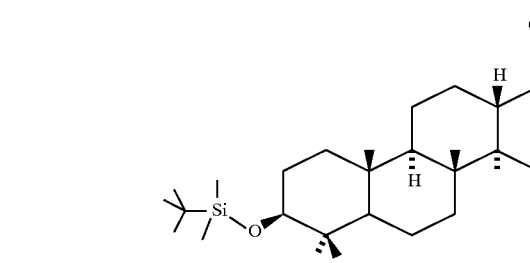

B

A solution of 12.0 g A (Phytochemistry loc. cit.) and 13.6 g imidazole in 450 mL dimethylformamide is treated under argon with 25.0 g t.-butyldimethylchlorosilane. The reaction mixture is stirred overnight at room temperature, diluted with diethylether and washed with aqueous 5% sodium hydrogencarbonate and brine. The organic layer is dried with sodium sulfate and the solvent removed under reduced pressure. Chromatography on silica (hexane/ethylacetate) gives the title compound B as a white foam.

$R_f$ (silica): 0.53 (hexane/ethylacetate 9:1)

$^1$H-NMR (CDCl$_3$) characteristic signals: 3.15 (1H,dd,J= $^5/_{12}$,H—C(3)), 2.65–2.45(1H,m,H—C(17)), 2.10 (3H,s, H$_3$CCO).

b) Process step 2, Scheme A

3μ-t.-Butyl-dimethylsiloxy-17-acetyl-hexanor-dammarane-enolacetate

B

C

A solution of 1.0 g p-toluenesulfonic acid hydrate in 200 mL acetic anhydride is heated to 140° C. for 30 min. At room temperature 3.0 g B is added and the reaction mixture is heated for 3 hrs. to 140° C. Acetic acid is slowly distilled off during the reaction period. The reaction mixture is concentrated to about 100 mL under reduced pressure, diluted with diethylether and extracted with cold aqueous 5% sodium hydrogen carbonate. The organic layer is dried with sodium sulfate and the solvent removed under reduced pressure. Flash chromatography on silica (hexane/ethylacetate, 95:5) gives the title compound C as a white solid (mixture of two diastereomeric enolacetates).

$R_f$ (silica): 0.41 (hexane/ethylacetate, 95:5)

$^1$H-NMR (CDCl$_3$) characteristic signals:3.15 (1H,dd,J= $^5/_{12}$,H—C(3)), 2.50–2.00 (3H,m,H—C(13),H$_2$—C(16)), 2.07 and 2.06 (3H,s,diastereomeric H$_3$CCOO).

c) Process steps 3+4, Scheme A

3β-t.-Butyl-dimethylsiloxy-17β-acetyl-hexanor-dammarane

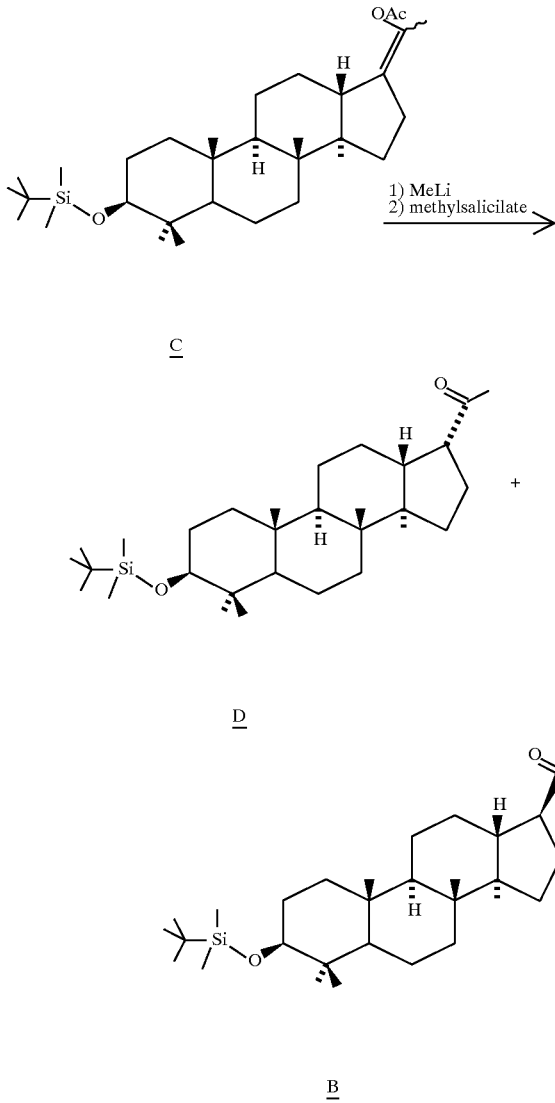

A solution of 445 mg C in 10 ml absolute diethylether is treated under argon with 3.75 mL 1.6M ether solution of methyllithium at 0° C. The reaction mixture is stirred for 1 hr. at 0° C., cooled to −78° C. and treated with 150 mg methylsalicylate. The reaction mixture is stirred for 30 min. at −78° C., treated with water and extracted with ethylether. The organic layer is dried with sodium sulfate and the solvent removed under reduced pressure. Chromatographic purification on silica (hexane/ethylacetate, 4:1)gives the title compound D as a white foam.

R$_f$ (silica): 0.34 alfa-ketone, 0.26 beta-ketone (hexane/ethylacetate, 95:5)

$^1$H-NMR (CDCl$_3$) characteristic signals: 3.15 (1H,dd,J= 5/12,H—C(3)), 3.00–2.94 (1H,m,H—C(17)), 2.11 (3H,s, H$_3$CCO).

d) Process step 5. Scheme A

3 β-t.-Butyl-dimethylsiloxy-20-trifluormethansulfonyloxy- 17α-hexanor-dammar-20-ene

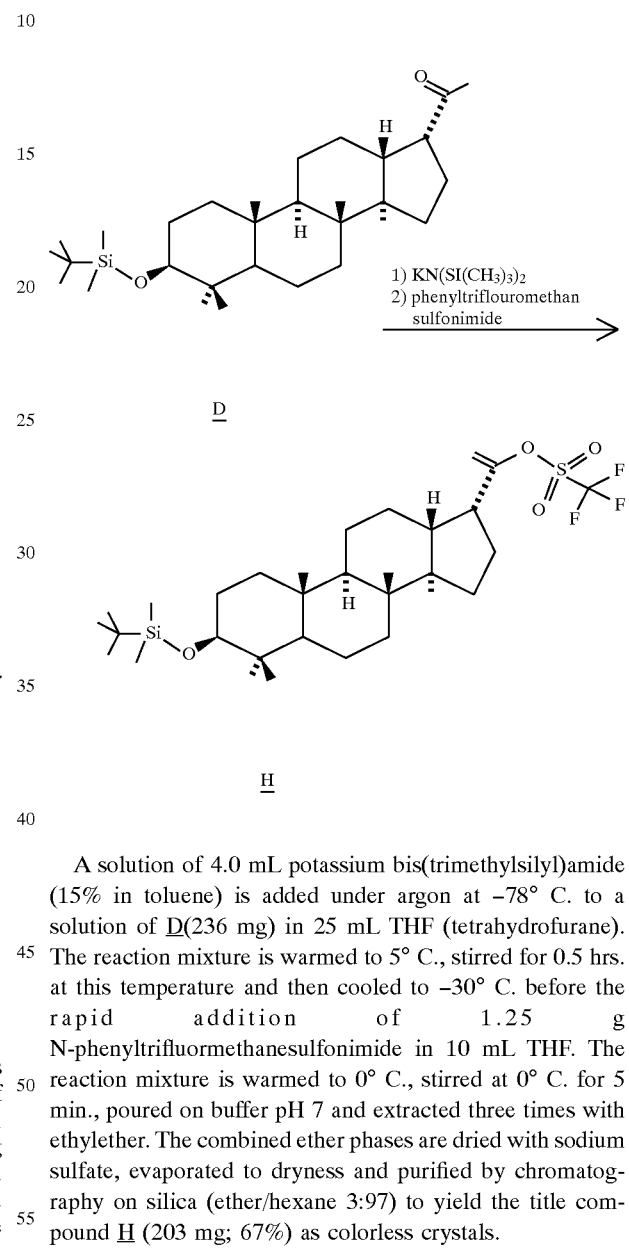

A solution of 4.0 mL potassium bis(trimethylsilyl)amide (15% in toluene) is added under argon at −78° C. to a solution of D(236 mg) in 25 mL THF (tetrahydrofurane). The reaction mixture is warmed to 5° C., stirred for 0.5 hrs. at this temperature and then cooled to −30° C. before the rapid addition of 1.25 g N-phenyltrifluormethanesulfonimide in 10 mL THF. The reaction mixture is warmed to 0° C., stirred at 0° C. for 5 min., poured on buffer pH 7 and extracted three times with ethylether. The combined ether phases are dried with sodium sulfate, evaporated to dryness and purified by chromatography on silica (ether/hexane 3:97) to yield the title compound H (203 mg; 67%) as colorless crystals.

$^1$H-NMR (360 MHz, CDC13); characteristic signals: 2.85–2.94 (bq, 1H, βH—C(17); 3.20 (dd, 1H, αH—C(3)); 5.12 (bd, 1H, J=4, H$_a$—C(21); 5.20 (d,1H,J=4 Hz, H$_b$—C(21).

e) Process step 6, Scheme A

3β-t.-Butyl-dimethylsiloxy-20-tri-n-butylstannyl-17α-hexanor-dammar-20-ene

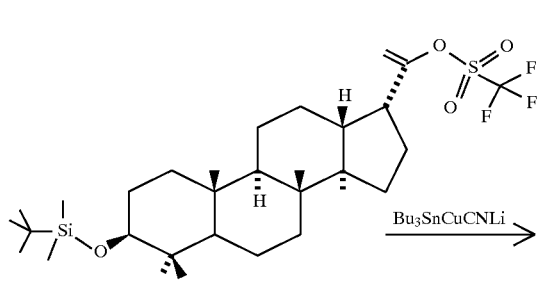

H

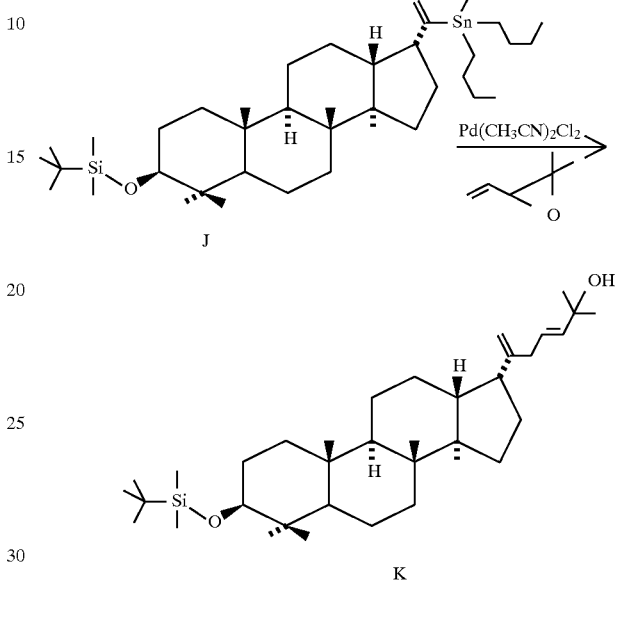

J

A solution of 44 mL n-BuLi (1.6N in hexane) is added at −78° C. to a suspension of 3.15 g CuCN in 200 mL THF under argon. After stirring at −50° C. for 10 min., the so obtained green solution is treated at −78° C. with 18.6 mL n-Bu₃SnH. After 10 min., 2.14 g vinyl triflate in 30 mL THF are added and the reaction mixture is stirred at −78° C. for 10 min., poured on 25% aq. NH₄Cl/hexane (0.75 l/0.5 l) under vigorous stirring, filtered from the precipitate and extracted three times with hexane. The combined organic phases are dried over Na₂SO₄, evaporated to dryness and purified by chromatography on silica (hexane), to give the title compound J (53%) as a colorless viscous oil.

$^1$H-NMR (360 MHz, CDCl₃); characteristic signals: 2.82–2.92 (bq,1H, βH—C(17); 3.14 (dd, 1H, αH—C(3); 5.18 (bs, 1H, H—C(21); 5.80 (bs, 1H, H—C(21).

f) Process step 7, Scheme A

3β-t.-Butyl-dimethylsiloxy-17α-23-(E)-dammara-20,23-diene-25-ol

J

K

A solution of 24 mg Pd(CH₃CN)₂Cl₂ in 0.3 mL H₂O and 12 mL DMF is added to a solution of 0.4 g 2,2-dimethyl-3-vinyloxirane (Tetrahedron, 1989, 45, 979) and 1.36 g J in 12 mL THF at room temperature. The reaction mixture is stirred overnight at room temperature. The slightly turbid yellow solutionias poured onto water and extracted with ethyl-ether. The combined organic phases are dried over Na₂SO₄ and evaporated to dryness to yield the title compound K as yellow waxy solid, which is used without further purification in the next step.

g) Process step 8, Scheme A (17α)-23-(E)-dammara-20,23-diene-3β,25-diol

K

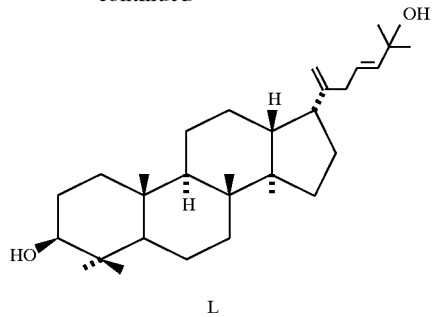

L

A solution of 1.45 g K in 60 mL THF is treated with 100 mL tetrabutylammonium fluoride (1M solution in THF) at 60° C. for 1.5 hrs. The reaction mixture is poured onto 1 l half saturated aqueous NaHCO₃-solution and extracted with ether. The combined organic phases are dried over $Na_2SO_4$, evaporated to dryness and purified by chromatography on silica (acetone/ether/hexane; 5/40/55) to yield 670 mg dammaradiendiol L (83% over two steps) as colorless crystals. A sample is recrystallized from ether/hexane. M.p.: 90.6°–91.4° C. $[\alpha]_{589}^{25}=-7.45°$. $[\alpha]_{302}^{25}=-119.2°$. $[\alpha]_{296}^{25}=-109.5°$. $[\alpha]_{280}^{25}=-38.7°$; (EtOH, c=1.06), The ¹H-NMR spectrum of the synthetic material is identical with the natural compound isolated from Palmyrah flour (*Borassus flabellifer* L.)

¹H-NMR (360 MHz, CDCl₃): ppm 0.73 (bd, 1H, J=12.5 and 1.3; H—C(5)); 0.78 (s, 3H, H—C(28)); 0.85 (s, 3H, H—C(19)); 0.90 (s, 3H, H—C(30)); 0.95 (s, 3H, H—C(18)); 0.98 (s, 3H, H—C(29)); 1.33 (s, 6H, H—C(26,27)); 1.19–1.74 (m, 15H, H—C(1,2,6,7,9,11,12,15 )); 1.75–1.84 (m, 2H, H—C(16)); 1.98–2.05 (m, 1H, H—C(13)); 2.59–2.64 (m, 1H, βH —C(17)); 2.66 (bd, 1H, J=6.3 Hz, H—C(22)); 2.79 (bs), 2.82 (dd, 1H, H—C(22)); 3.18–3.23 (m, 1H, αH—C(3)); 4.88 (s, 1H, H—C(21)); 4.95 (s, 1H, H—C(21)); 5.59–5.62 (m, 2H, H—C(23,24)).

EXAMPLE 2'

The compound (17β)-23E-dammara-20,23-dien-3β,25-diol may be prepared analogously starting from the compound A and proceeding analogously to steps a) and d) to g) of EXAMPLE 2. Physical data for the product are as hereinafter described in EXAMPLE 3.

EXAMPLE 3

Synthesis of (17β)-23E-dammara-20,23-diene-3β, 25-diol (β-EPIMER OF COMPOUND OF FORMULA IC)

a) Process step 9, Scheme B

3β-t.-Butyl-dimethylsiloxy-17β-acetyl-hexanor-dammarane-trisylhydrazone

A suspension of 1.6 g B (produced as in EXAMPLE 2a) and 3.3 g 2,4,6-triisopropylbenzenesulfonic acid hydrazide in 50 mL acetonitrile is treated with 150 uL conc. HCl at room temperature. The suspension is stirred during 30 min. at room temperature, diluted with ethylether and washed with aqueous 5% sodiumhydrogencarbonate solution. The organic layer ias dried with sodium sulfate and the solvent removed under reduced pressure. Chromatography on silica

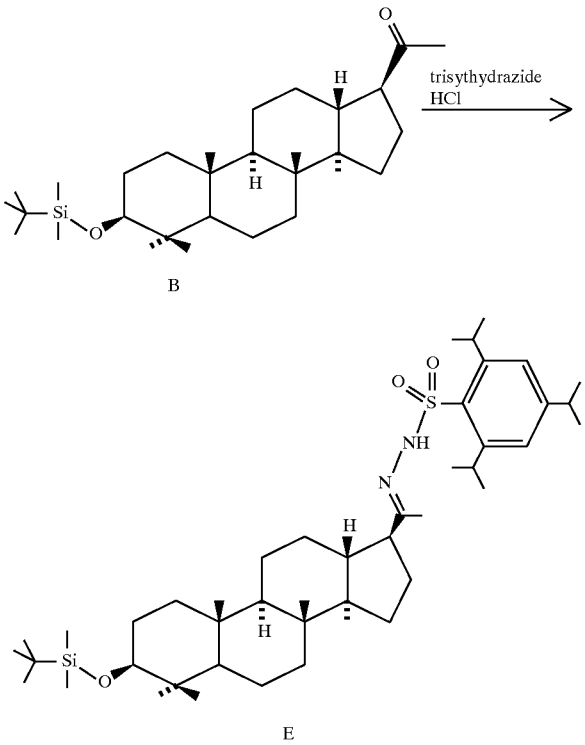

(hexane/ethylacetate, 4:1) gives the title compound E as a white amorphous foam (mixture of e/z diastereomers).

$R_f$ (silica): 0.61 (hexane/ethylacetate, 4:1)
¹H-NMR (CDCl₃) characteristic signals: 7.24 and 7.12 (3H,s,H—C(arom.)),4.22–4.08 (2H,m,H—C—C(arom.)), 3.15–3.05 (1H,m, H—C(3)), 2.92–2.78 (1H,m,H—C—C (arom.)), 2.35 –2.22 (1H,m,H—C(17)),1.67 (1H,s,H₃CCN).
b) Process steps 10+7, Scheme B 3β-t.-Butyl-dimethylsiloxy-17β-23-(E)-dammara-20, 23-diene-25-ol

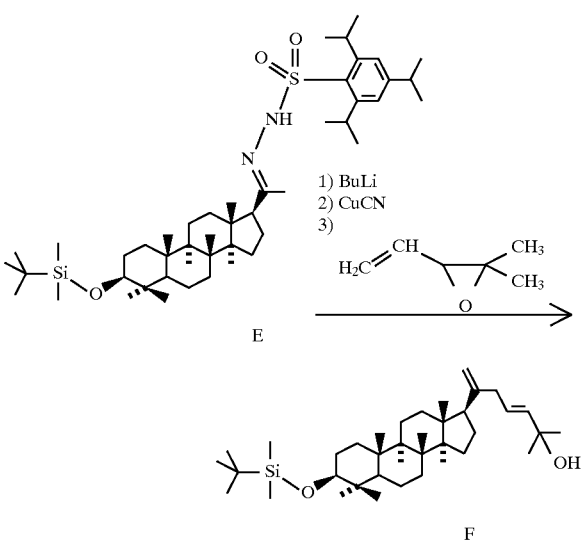

A solution of 161 mg E in 5 mL absolute diethylether is treated at −78° C. under argon with a solution of 0.5 mL 1.6M butyllithium in hexane. The yellow/brown solution is stirred at −20° C. until gas evolution is complete. After the addition of 15 mg cuprous cyanide at −78° C., 160 uL of 1,1-dimethyl-2-vinylepoxide is added and the reaction mixture is stirred at −20° C. for 2 hrs. The reaction mixture is diluted with diethylether and treated with aqueous saturated ammonium chloride (pH=9) solution. The organic layer is dried with sodium sulfate and the solvent removed under reduced pressure to yield 190 mg of an amorphous solid. This material is directly used without further purification for the removal of the silyl protecting group.

c) Process step 8, Scheme B (17β)-23-(E)-dammara-20,23-dien-3β,25-diol

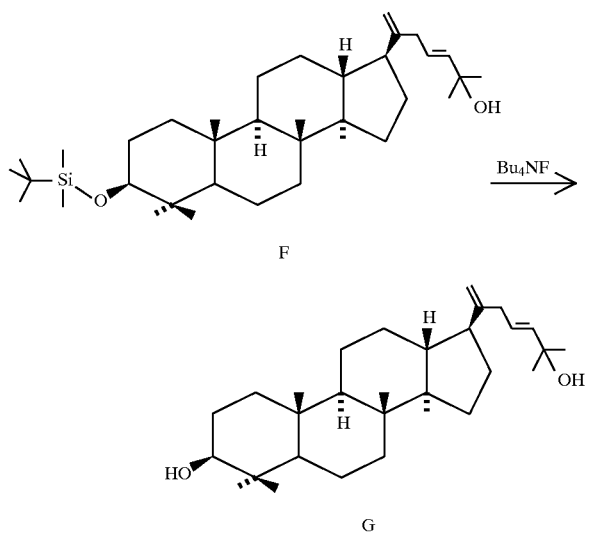

A solution of 190 mg silylether F in 5 mL absolute THF is treated under argon with 1 mL of 1M tetrabutylammoniumfloride solution in THF. The reaction mixture is stirred for 12 hrs. at 50° C., diluted with diethylether and extracted with aqueous sodiumhydrogencarbonate solution. Removal of solvent and chromatography on silica (hexane/ethylacetate, 4:1) gives 35 mg of the title compound as a crystalline white product.

$^1$H-NMR (CDCl$_3$) characteristic signals: 5.60–5.50 (2H, m, H—C(23+24)), 4.70 (1H,s,H—C(21)), 4.62 (1H,s,H—C (21)), 3.13 (1H,dd,J=5/1, H—C(3)), 2.65–2.55 (2H,m,H—C (22)), 2.18–2.12 (1H,m,H—C(17)).

EXAMPLE 3'

The compound (17(α)-23E-dammara-20,23-diene-3β,25-diol may be prepared analogously starting from the compound D of EXAMPLE 2c) and proceeding analogously to steps a) through c) of EXAMPLE 3, i.e. via the following intermediates:

3β-t.Butyl-dimethylsiloxy-17α-acetyl-hexanor-dammarane-trishydrazone; and

3β-t.Butyl-dimethylsiloxy-17α-23-(E)-dammara-20,23-diene-25-ol.

Physical data for the product compound are as hereinbefore described in EXAMPLE 2.

As previously indicated, doses of dammara compounds for use in accordance with the present invention will vary, e.g. depending on the route of administration, the condition to be treated and, in particular, the specific dammara compound employed. ED$_{50}$ values obtained for the 17α-dammara compound of formula IC, and its 17β-epimer [(17β)-23-(E)-dammara-20,23,dien-3β,25-diol] in one trial run in accordance with tests 9 and 10 hereinbefore described, together with typical results for the known antiinflammatory/immunosuppressive agent cyclosporin A are as follows

|  | TEST 9 (DTH) [ED$_{50}$] | TEST 10 (SLE) [ED$_{100}$] |
|---|---|---|
| FORMULA IC | 4.0 μg/kg p. o. | 10 μg/kg p. o. |
| β-EPIMER OF IC COMPOUND | 10 mg/kg p. o. | 10 mg/kg p. o. |
| CYCLOSPORIN A | 45–50 mg/kg p. o. | 75–100 mg/kg p. o. |

Indicated oral doses for antiinflammatory and immunosuppressive use, e.g. for use in autoimmune disease therapy, will thus be:

in the case of the formula IC compound, of the order of one thousandth to one tenthousandth of those indicated using cyclosporin A therapy, e.g. of about 0.4 or 0.5 to 4.0 or 5.0 μg/kg/day in the case of the 17β-epimer of the formula IC compound, of the order of ¼ to ¹⁄₁₀th of those indicated using cyclosporin A therapy, e.g. of about 0.4 or 0.5 to 1.0 or 1.25 mg/kg/day.

We claim:

1. A 17 α-carbonyl-dammara compound containing the ring system of formula

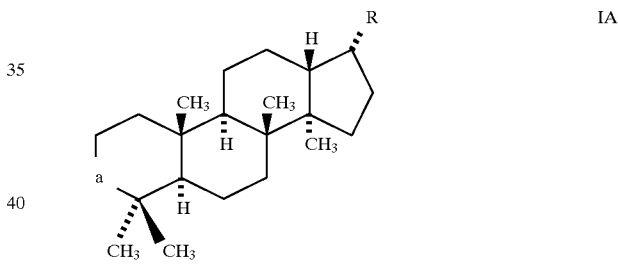

wherein a is >CH—OR$_1$, in which R$_1$ is hydrogen or a physiologically cleavable and acceptable acyl residue, or C=O and R is a C$_{1-8}$aliphatic group, said ring system optionally containing unsaturation and optionally further substituted.

2. A compound according to claim 1 of formula IB

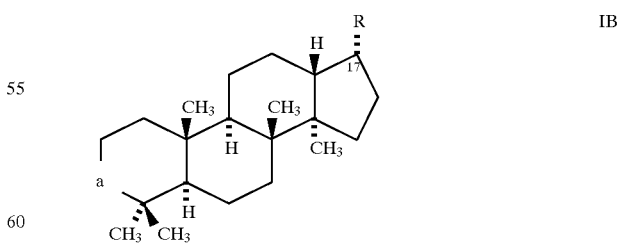

wherein a is >CH—OR$_1$, in which R$_1$ is hydrogen or a physiologically cleavable and acceptable acyl residue, or >C=O and R is a C$_{1-8}$aliphatic group optionally comprising one or two double bonds and optionally substituted with at least one hydroxy group.

3. A compound according to claim 1 of formula XII b

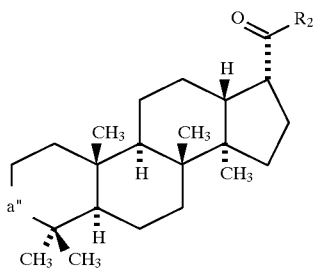

wherein a" is >CH—OH or >C=O in free or protected form and the substituent at the 17 position, $R_2CO—$ is an $C_{1-4}$ acyl group.

4. A 17 α-carbonyl-dammara compound of formula IA

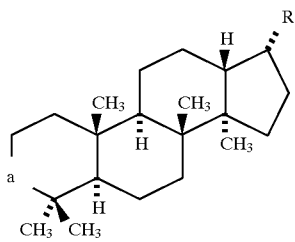

wherein a is >CH—$OR_1$, in which $R_1$ is hydrogen or a physiologically cleavable and acceptable acyl residue, or >C=O and R is a group attached to the carbon atom at the 17-position by a carbon atom.

5. A 17 α-carbonyl-dammara compound of formula IA

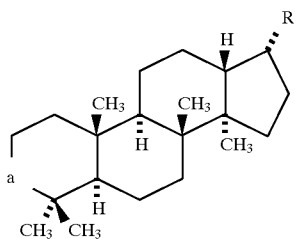

wherein a is >CH—$OR_1$, in which $R_1$ is hydrogen or a physiologically cleavable and acceptable acyl residue, or >C=O and R is a $C_{1-8}$ aliphatic group optionally comprising one or two double bonds and optionally substituted with at least one hydroxy group.

6. A 17 α-carbonyl-dammara compound according to claim 5 wherein R is a $C_8$ aliphatic group optionally comprising one or two double bonds an optionally substituted with at least one hydroxy group.

7. A 17 α-carbonyl-dammara compound according to claim 1 wherein said $C_{1-8}$ aliphatic group comprises one or two double bonds.

8. A 17 α-carbonyl-dammara compound according to claim 1 wherein said C1–8 aliphatic group is substituted with at least one hydroxy group.

9. A pharmaceutical composition comprising a 17 α-dammara compound according to claim 1 in combination with a pharmaceutically acceptable diluent or carrier.

10. A method of treating a subject in need of immunosuppressant or antiinflammatory therapy which comprises administering an effective amount of a 17 α-dammara compound as defined in claim 1 to said subject.

11. A compound according to claim 1 which is the compound of formula IC [(17 α)-23-(E)-dammara-20,23-dien-3β,25-diol]

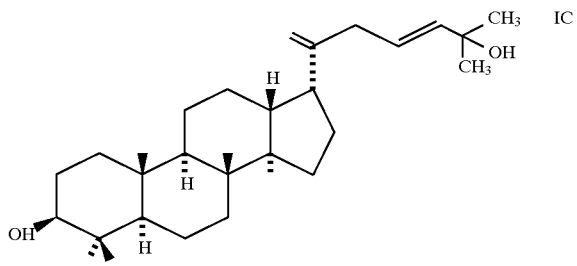

or physiologically hydrolysable and acceptable ester thereof.

12. A compound of formula XIIIa

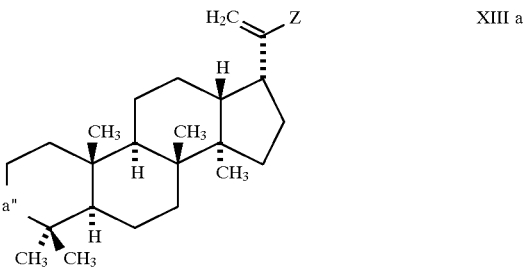

wherein a" is >CH—OH or >C=O in free or protected form and Z is an alkali metal atom or a trialkyl tin group.

13. A compound as claimed in claim 12 wherein Z is lithium or tri-$C_{1-4}$ alkyl tin.

14. A process for the production of a 17 α-dammara compound which process comprises a) epimerising a 17 β-carbonyl-dammara compound to obtain a 17 α-carbonyl-dammara compound and, optionally b) further derivatizing said 17 α-carbonyl-dammara compound.

15. A process for the production of 17 α-$C_{1-8}$ aliphatic-dammara compound which comprises coupling a 17-carbonyl-dammara compound, in protected form as required, with an electrophile and, if desired, removing protecting groups and functionalities.

* * * * *

UNITED STATES PATENT AND TRADEMARK OFFICE
CERTIFICATE OF CORRECTION

PATENT NO.    : 5,852,005                                       Page 1 of 1
DATED         : December 22, 1998
INVENTOR(S)   : Hiestand et al.

It is certified that error appears in the above-identified patent and that said Letters Patent is hereby corrected as shown below:

Under column 5/6, delete structure V between steps 3 and 4 and replace with following structure:

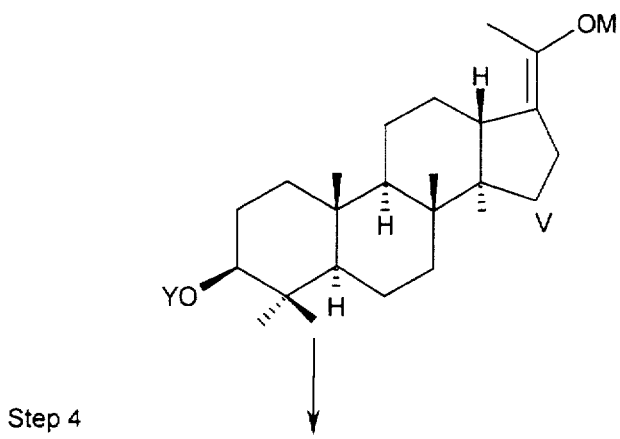

Step 4

Column 32,
Claim 1, delete --carbonyl- --.

Column 33,
Claim 4, delete --carbonyl- --.
Claim 5, delete --carbonyl- --.

Signed and Sealed this

Ninth Day of October, 2001

Attest:

NICHOLAS P. GODICI
Attesting Officer      Acting Director of the United States Patent and Trademark Office